United States Patent [19]

Jamieson et al.

[11] Patent Number: 5,087,636

[45] Date of Patent: Feb. 11, 1992

[54] METHOD TO DESTROY MALIGNANT CELLS IN MONONUCLEAR CELL POPULATIONS

[75] Inventors: Catriona Jamieson, West Vancouver; Julia G. Levy, Vancouver, both of Canada

[73] Assignee: University of British Columbia, Vancouver, Canada

[21] Appl. No.: 482,942

[22] Filed: Feb. 20, 1990

[51] Int. Cl.$^5$ .............................................. A61K 31/40
[52] U.S. Cl. ........................................ 514/410; 424/9; 514/2; 540/145
[58] Field of Search .................... 540/145; 514/410, 2; 424/9

[56] References Cited

U.S. PATENT DOCUMENTS 4,883,790  11/1989  Levy et al. ........................ 540/145
4,920,143   4/1990  Levy et al. ........................ 514/410

OTHER PUBLICATIONS

Gale et al., *Seminars in Hematology* (1987) 24:40–54.
Champlin et al., *Seminars in Hematology* (1987) 24:55–67.
Champlin et al., *Seminars in Hematology* (1988) 25:74–80.
Malik et al., *Brit. J. Cancer* (1987) 56:589–595.
Sieber et al, *Blood* (1986) 68:32–36.
Sieber et al., *Photochem. Photobiol.* (1987) 46:71–76.
Singer et al., *Brit. J. Hematol.* (1988) 68:417–422.
Talpaz et al., *Seminars in Hematology* (1988) 25:62–73.
Jamieson et al., *SPIE Photodynamic Therapy: Mechanisms* (1989) 1065:152–163.

*Primary Examiner*—Richard L. Raymond
*Attorney, Agent, or Firm*—Kate H. Murashige

[57] ABSTRACT

A method to prepare bone marrow or other hemopoietic cells free of malignant cells for autologous transplants is described. The mononuclear cells from the marrow are treated with a green porphyrin (Gp) to effect the uptake of said Gp by malignant cells selectively, and then irradiated with a wavelength of light absorbed by said Gp to effect the destruction of the malignant cells. The purged marrow cells can then be used for autologous transplantation.

37 Claims, 8 Drawing Sheets

BPD-DA

BPD-DB

BPD-MA

BPD-MB

METHOD TO DESTROY MALIGNANT CELLS IN MONONUCLEAR CELL POPULATIONS

TECHNICAL FIELD

The invention relates to medical applications of photodynamic therapy. More specifically, it concerns the use of specific porphyrin-derived compounds for the destruction of malignant cells such as leukemic cells in the presence of normal cells in preparations of mononuclear cells such as those prepared from bone marrow.

BACKGROUND ART

Autologous bone marrow transplantation has been employed to maintain a state of remission in patients with various malignancies, including leukemia. In this procedure, bone marrow of a patient having a malignancy is removed during remission and stored for readministration after the patient relapses into the active presence of the cancer (Gale, R. P. et al., *Seminars in Hematology* (1987) 24:40-54). As autologous marrow is used, it is not necessary to provide HLA-matched donors (which limits allogenic bone marrow transplants to 6% of the adults with acute myelogenous leukemia (AML)); however, a significant drawback for autologous marrow is that malignant cells may remain in the putatively remitted marrow. There have been a number of attempts to purge remission marrow of residual malignant cells, but these attempts have been less than successful (Champlin R., et al., *Seminars in Hematology* (1987) 24:55-67; Champlin, R. E., et al., *Seminars in Hematology* (1988) 25: 74-80; Malik, Z., et al., *Brit J Cancer* (1987) 56:589-595). The Malik paper describes the destruction of leukemic cells by photoactivation of endogenous porphyrins. In addition, certain amphipatic dyes have been reported to photosensitive leukemic cells to a greater extent in comparison to normal mononuclear cells (Sieber, F., et al., *Blood* (1986) 68:32-36; Sieber, F., et al., *Photochem Photobiol* (1987) 46:71-76; Singer, C. R. J., et al., *Brit J Hematol* (1988) 68:417-422; Tulpaz, M., et al., *Seminars in Hematology* (1988) 25:62-73).

Compounds useful in the technique of the present invention are described in copending U.S. Ser. No. 07/414,201 filed Sept. 28, 1989 and incorporated herein by reference. These compounds are hydrobenzo derivatives of hematoporphyrin which absorb longer wavelength light, in the range of approximately 670-780 nm, than does hematoporphyrin or alternative medically useful derivative forms. These green porphyrin compounds also exhibit a fluorescence excitation peak at shorter wavelengths which can be used for fluorescence emission in diagnosis. Photoactivation of compounds of this type for the destruction of solid tumors and of infectious organisms is also described.

DISCLOSURE OF THE INVENTION

The invention provides an effective method to purge hemopoietic cells, such as mononuclear cells from bone marrow, of malignant cells. Application of this method permits the use of autologous marrow from patients in remission from the malignancy for subsequent replacement upon relapse. The invention also provides an effective method to purge malignant cells from the bone marrow or other hemopoietic cells of leukemia patients with active disease (not in remission) or from patients with other (nonleukemic) malignancies who would benefit from the same purging procedure. The method employs photoactivation of green prophyrins added to the hemopoietic cells.

Accordingly, in one aspect, the invention is directed to a method selectively to destroy malignant cells in compositions of hemopoietic cells, such as those of bone marrow, which method comprises contacting said cells with a green porphyrin (Gp), as herein defined, for a time sufficient to cause uptake of the Gp by malignant cells, removing excess Gp from the cell preparation, followed by irradiation of the resulting composition with a wavelength of radiation absorbed by said Gp at an intensity and for a time effective to destroy malignant cells, but otherwise maintaining the hemopoietic power of the remaining cells.

In another aspect, the invention is directed to a method to confirm the absence of or detect the presence of malignant cells in a bone marrow or other hemopoietic cells composition, which method comprises contacting the cell composition with the herein described Gp, as described above, irradiating at an excitation wavelength and detecting the presence or absence of fluorescence ascribable to the Gp absorbed by any malignant cells present.

BRIEF DESCRIPTION OF THE DRAWINGS

FIGS. 2-1 to 2-4 show the structures of four preferred forms of the hydro-monobenzoporphyrin derivatives of the formulas 3 and 4 (BPD).

FIG. 4 shows the correlation of the fluorescence of leukemic cells with the presence of marker green dye.

FIGS. 5-7 show the results of FACS analysis of leukemic vs. normal cells.

MODES OF CARRYING OUT THE INVENTION

The invention provides treatment of the hemopoietic cells such as those in bone marrow with certain porphyrin derivatives for therapy or diagnosis.

Procedures for withdrawal and replacement of bone marrow from the patient are generally known in the art. The herein invention resides in a method to purge the marrow ex vivo selectively of malignant cells, and to detect malignant cells in such composition.

Gp Compounds Useful in the Invention

Figure 1:
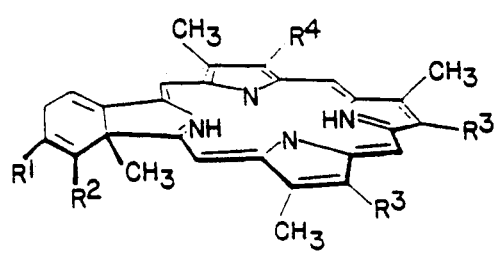
FIGS. 1-1 to 1-6 show the structure of the green porphyrin (Gp) compounds used in the methods of the invention.
Figures 1, 2:
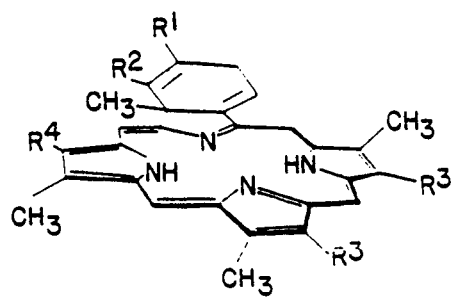

The compounds useful in the method of the invention, in general, have the structures shown in FIG. 1. These compounds are prepared by Diels-Alder reaction involving one of the conjugated systems of hematoporphyrin with an acetylene-derivative dienophile which results in a fused cyclohexadiene, referred to herein as "hydro-benzo" fused to the A or B ring as shown in formulas 1 and 2 of FIG. 2. Rearrangement of the $\pi$ system in the hexadiene ring results in the compounds of formulas 3 and 4; reduction provides the compounds of formulas 5 and 6. While all of the compounds shown in FIG. 1 are useful in the invention, those formulas 3 and 4 are preferred. Particularly preferred forms of these compounds are shown in FIG. 2.

As used herein, green porphyrin (Gp) refers to the compounds described in FIG. 1 generically. Hydromonobenzoporphyrin derivative (BPD) is generally used to refer to the compounds of formulas 3 and 4 of FIG. 1 and those shown in FIG. 2 since these are the preferred forms of Gp.

Specific preparation of some compounds useful in the invention or their precursors is described by Morgan, A. R., et al., *J Chem Soc Chem Commun* (1984) pp. 1047-1048; and by Pangka, B. S. et al., *J Organic Chem* (1986) 51:1094. As described in these publications, it had earlier been reported that protoporphyrin-IX dimethyl ester, when reacted with strong Diels-Alder dienophile reagents such as tetracyanoethylene, is derivatized to the hydro-dibenzo derivatives. However, it is clear that, as shown by these references, when acetylene is derivatized with more weakly electron withdrawing groups and used as a Diels-Alder reagent, hydro-monobenzo derivatives are formed. Thus, there are obtained directly from reaction of protoporphyrin with, for example dimethyl acetylene dicarboxylate (DMAD), compounds shown as formulas 1 and 2 of FIG. 1, wherein $R^1$ and $R^2$ represent the substituents on the original acetylene-derived Diels-Alder reagent, $R^1C\equiv CR^2$— in this case, carbomethoxy. $R^1$ and $R^2$ are, generally, specifically carbalkoxy groups such as carbomethoxy or carboethoxy. $R^3$ represents substituents present on the porphyrin used in the reaction or substituents derived therefrom. In the Morgan reference, the reaction substrate was protoporphyrin-IX dimethyl ester; thus the ligand $R^3$ was, in all cases, 2-carbomethoxyethyl.

The disclosed substituents in the Morgan and Pangka references for the acetylene-derived dienophile include phenylsulfonyl—i.e., $SO_2Ph$, either as a single substituent, as described in the foregoing references (β-phenylsulfonylpropiate) or, putatively, wherein both $R^1$ and $R^2$ are sulfonyl derivatives. In general, $R^1$ and $R^2$ are each, independently, moderate electron-withdrawing substituents, and are, more commonly, carbalkoxy, or alkyl or aryl sulfonyl, or any other activating substituents, which are not sufficiently electron-withdrawing to result in reaction with both A and B rings rather than reaction with only one, such as cyano or —CONR$^5$CO— wherein $R^5$ is aryl or alkyl. One of $R^1$ and $R^2$ may optionally be H while the other is an electron withdrawing substituent of sufficient strength to facilitate the Diels-Alder reaction.

As used herein, carboxy is, as conventionally defined, —COOH and carbalkoxy is —COOR, wherein R is alkyl; carboxyalkyl refers to the substituent —R'—COOH wherein R' is alkylene; carbalkoxyalkyl refers to —R'—COOR where R' and R are alkylene and alkyl respectively. Alkyl is a saturated straight or branched chain hydrocarbyl of 1-6 carbon atoms such as methyl, n-hexyl, 2-methylpentyl, t-butyl, n-propyl, and so forth. Alkylene is as alkyl except that the group is divalent. Aryl or alkyl sulfonyl moieties have the formula $SO_2R$ wherein R is alkyl as above-defined, or is aryl, wherein aryl is phenyl optionally substituted with 1-3 substituents independently selected from halo (fluoro, chloro, bromo or iodo), lower alkyl (1-4C) or lower (1-4C). In addition, one or both $R^1$ or $R^2$ can itself be aryl—i.e., phenyl optionally substituted as above-defined.

As shown in FIG. 1, the adduct formed by the reaction of $R^1$—C≡C—$R^2$ with the protoporphyrin-IX ring system ($R^3$ is a protected form of 2-carboxyethyl such as 2-carbomethoxyethyl or 2-carboethoxyethyl; $R^4$ is CH=CH$_2$) are compounds of the formulas 1 and 2 wherein the compound is formula 1 results from addition to the A ring and formula 2 results from addition to the B ring. In these resulting products of formulas 1 and 2, $R^4$ remains CH=CH$_2$, however this vinyl group is readily derivatized to other embodiments of $R^4$ by addition to or oxidation of the vinyl ring substituent of ring B in formula 1 or ring A in formula 2. The addition or oxidation products can be further substituted if the added substituents are functional leaving groups—for example —Br may be substituted by —OH, —OR (R is alkyl 1-6C as above), or —NH$_2$, —NHR, —NR$_2$, etc. In preferred embodiments, one of the added substituents is hydrogen, and the other is selected from the group consisting of halo (fluoro, chloro, bromo or iodo), hydroxy, lower alkoxy, amino or an amide, sulfhydryl or an organosulfide or can be, itself, hydrogen. Addition to the vinyl group does not appreciably change the absorption spectrum of the resulting compound. The product of the Markovnikov addition of water provides a substituent structure analogous to the hematoporphyrin ring system at the relevant ring. Thus, the compounds of the invention include various groups as $R^4$, including substituents which provide additional prophyrin or prophyrin-related ring systems, as will be further described below.

$R^3$ in protoporphyrin-IX is 2-carboxyethyl (—CH$_2$CH$_2$COOH). However, the nature of $R^3$ (unless it contains a π-bond conjugated to ring π-bond), is ordinarily not relevant to the progress of the Diels-Alder reaction or the to the effectiveness and absorption spectrum of the resulting product. $R^3$ can thus be, for example, lower alkyl (1-4C), or ω-carboxyalkyl (2-6C) or the esters or amides thereof. The $R^3$ substituent may also be substituted with halogen as above-defined, or with other non-reactive substituents. However, as the convenient starting materials for the Gp compounds of the invention are the naturally occurring porphyrins, the preferred substituents for $R^3$ are CH$_2$CH$_2$COOH or —CH$_2$CHR$_2$COOR, wherein R is alkyl (1-6C).

It should be noted that while the nature of the $R^3$ substituent does not ordinarily influence the course of the Diels-Alder reaction by altering the nature of the diene substrate, derivatization may be necessary to promote the reaction by providing suitable solubility characteristics or to prevent interference with the reaction. Thus, the Diels-Alder reactions described by Morgan et al. and by Pangka et al. utilized the dimethylester of protoporphyrin-IX as a substrate in order to prevent interference with the reaction by the free carboxyl group and to provide suitable solubility characteristics.

In the BPD compounds of the invention, it has been found advantageous to hydrolyze or partially hydrolyze the esterified carboxy group in —CH$_2$CH$_2$COOR. The hydrolysis occurs at a much faster rate than that of the ester groups of $R^1$, $R^2$, and the solubility characteristics of the resulting compounds are more desirable than those of the unhydrolyzed form. Hydrolysis results in the diacid or monoacid products (or their salts).

The hydro-monobenzoporphyrins which directly result from the Diels-Alder reaction described in the cited references can also be isomerized as therein described (see Morgan et al. and Pangka et al. (supra)) to compounds of formulas shown as 3 and 4 of FIG. 1 by treatment with suitable reagents such as triethylamine (TEA) in methylene chloride or 1,5-diaza bicylo [5.4.0] undec-5-ene (DBU). The stereochemistry of the product is determined by the choice of reagent.

The depictions of compounds 3 and 4 in FIG. 1 do not show the relative position of the exocyclic methyl group (ring A of formula 3 and ring B of formula 4) with respect to the $R^2$ substituent. It has been found by these authors that rearrangement using TEA gives cis geometry for the angular methyl group and $R^2$, while treatment with DBU results in the trans product. This cis product is evidently kinetically controlled since treatment of the cis product with DBU results in a further rearrangement to trans stereochemistry. Thus, formulas 3 and 4 of FIG. 1 show the rearranged products generically, from either TEA or DBU catalyzed rearrangement in rings A and B respectively.

In addition, the Diels-Alder products can be selectively reduced by treating with hydrogen in the presence of palladium on charcoal to give the saturated ring analogs, shown as formulas 5 and 6 in FIG. 1, corresponding to the respective Diels-Alder products of rings A and B. These reduced products are less preferred embodiments, and are less useful in the method of the invention than the compounds of formulas 1-4.

The description set forth above with respect to the compounds of formulas 1 and 2 concerning derivatization by conversion of the remaining vinyl substituent ($R^4$) and with respect to variability of —$R^3$ applies as well as to the compounds of formulas 3, 4, 5 and 6.

The compounds of formulas 3 and 4 (BPD), and especially those which have hydrolyzed and partially hydrolyzed carbalkoxy groups in $R^3$, are most preferred. Compounds of the invention which contain —COOH may be prepared as the free acid or in the form of salts with organic or inorganic bases.

It will be noted that many of the compounds of FIG. 1 contain at least one chiral center and therefore exist as optical isomers. The conjugates and methods of the invention include compounds having both configurations of the chiral carbons, whether the compounds are supplied as isolates of a single stereoisomer or are mixtures of enantiomers and/or disastereomers. Separation of mixtures of diastereomers may be effected by any conventional means; mixtures of enantiomers may be separated by usual techniques of reacting them with optically active preparations and separating the resulting diastereomers.

It should further be noted that the reaction products may be unseparated mixtures of A and B ring additions, e.g., mixtures of formulas 1 and 2 or 3 and 4 or 5 and 6. Either the separated forms—i.e., formula 3 alone or 4 alone, or mixtures in any ratio may be employed in the methods of therapy and diagnosis set forth herein.

The name "dihydro"-monobenzoporphyrin describes the direct and rearrangement products of the Diels-Alder reaction of the porphyrin ring system with $R^1C\equiv C-R^2$; "tetrahydro"-monobenzoporphyrin describes the foregoing reduced products of formulas 5 and 6, and "hexahydro"-monobenzoporphyrin describes the analogs containing the exocyclic "benzo" ring completely reduced. Hydro-monobenzoporphyrin is used generically to include all three classes of oxidation state. The monobenzoporphyrins per se are outside the scope of the invention as their absorption maxima do not fall within the required range.

FIG. 2 shows four particularly preferred Gp compounds. These compounds are collectively designated benzoprophyrin derivative (BPD) as they are forms of Gp having the formula 3 or 4. These are hydrolyzed or partially hydrolyzed forms of the rearranged products of formula 3 and 4, wherein one or both of the protected carboxyl groups of $R^3$ are hydrolyzed. The ester groups at $R^1$ and $R^2$ hydrolyze relatively so slowly that conversion to the forms shown in FIG. 2 is easily effected.

For purposes of this description, $R^3$ is —$CH_2CH_2COOR^{3'}$. As shown in FIG. 2, each $R^{3'}$ is H in preferred compound BPD-DA, $R^1$ and $R^2$ are carbalkoxy, and derivatization is at ring A; BPD-DB is the corresponding compound wherein derivatization is at ring B. BPD-MA represents the partially hydrolyzed form of BPD-DA, and BPD-MB, the partially hydrolyzed form of BPD-DB. Thus, in these latter compound, $R^1$ and $R^2$ are carbalkoxy, one $R^{3'}$ is H and the other $R^{3'}$ is alkyl (1-6C). The compounds of formulas BPD-MA and BPD-MB may be homogeneous wherein only the C ring carbalkoxyethyl or only the D ring carbalkoxyethyl is hydrolyzed, or may be mixtures of the C and D ring substituent hydrolyzates. In addition, mixtures of any two or more of BPD-MA, —MB, —DA and —DB may be employed in the method of the invention.

As these hydrolyzed forms of the Diels-Alder product are previously undisclosed, the invention is also directed to these compounds. Thus, in another aspect, the invention is directed to compounds of the formulas shown in FIG. 2 wherein $R^1$ and $R^2$ are as above defined, and R is alkyl (1-6C). Preferred are embodiments wherein $R^1$ and $R^2$ are carbalkoxy, especially carbomethoxy or carboethoxy.

Certain other embodiments wherein $R^4$ is other than vinyl or wherein $R^3$ is a non-native substituent are also not disclosed in the art and the invention is directed to them, i.e., the invention is directed to the compounds shown in FIG. 1 wherein each $R^1$ and $R^2$ is independently selected from the group consisting of carbalkoxy (2-6C), alkyl (1-6C) sulfonyl, aryl (6-10C) sulfonyl, aryl (6-10C); cyano; and —$CONR^5$ CO— wherein $R^5$ is aryl (6-10C) or alkyl (1-6C);

each $R^3$ is independently carboxyalkyl (2-6C) or a salt, amide, ester or acylhydroazone thereof, or is alkyl (1-6C); and $R^4$ is $CHCH_2$, $CHOR^{4'}$, —CHO, —$COOR^{4'}$, $CH(OR^{4'})CH_3$, $CH(OR^{4'})CH_2OR^{4'}$, —$CH(SR^{4'})CH_3$, —$CH(NR^{4'}_2)$ $CH_3$, —$CH(CN)CH_3$, —CH($COOR^{4'})CH_3$, —$CH((OOCR^{4'})CH_3$, —$CH(halo)CH_3$, or —$CH(halo)CH_2(halo)$, wherein $R^{4'}$ is H, alkyl (1-6C) optionally substituted with a hydrophilic substituent, or wherein $R^4$ is an organic group of <12C resulting from direct or indirect derivatization of vinyl, or wherein $R^4$ is a group containing 1-3 tetrapyrrole-type nuclei of the formula —L—P as herein defined;

wherein when $R^4$ is $CHCH_2$, both $R^3$ cannot be 2-carbalkoxyethyl.

Compounds of the formulas 3 and 4 and mixtures thereof are particularly preferred. Also preferred are those wherein $R^1$ and $R^3$ are the same and are carbalkoxy, especially carboethoxy; also preferred are those wherein $R^4$ is —$CHCH_2$, $CH(OH)CH_3$ or —$CH(halo)$ $CH_3$, or is a group containing 1-3 tetrapyrrole-type nuclei of the formula —L—P (defined below).

As used herein, "tetrapyrrole-type nucleus" represents a four-ring system of the skeleton;

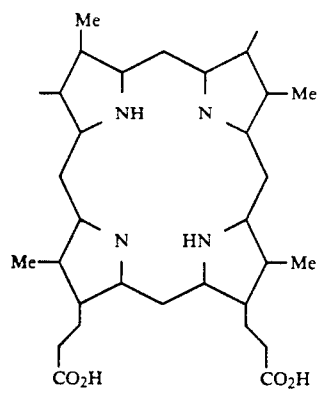

which is abbreviated $$\begin{array}{c} -A-B- \\ | \quad | \\ C-D \end{array}$$

and a salt, ester, amide or acylhydrazone thereof, which is highly conjugated. It includes the porphyrin system, which is, in effect, a completely conjugated system, the chlorin system, which is, in effect, a dihydro form of the porphyrin, and the reduced chlorin system, which is a tetrahydro form of the completely conjugated system. When "porphyrin" is specified, the completely conjugated system is indicated; Gp is effectively a dihydro form of the porphyrin system.

One group of compounds of the invention is that wherein the substituent $R^4$ includes at least one additional tetrapyrrole-type nucleus. The resulting compounds of the invention are dimers or oligomers in which at least one of the tetrapyrrole-type ring systems is Gp. Linkage between the Gp moiety through the position of $R^4$ to an additional tetrapyrrole-type ring system may be through an ether, amine or vinyl linkage. Additional derivatization in the case of porphyrin ring systems which have two available substituent positions (in both A and B rings) corresponding to $R^4$ can also be formed, as further described below.

As stated above, the compounds of formulas shown in FIG. 1 include those wherein the embodiment of $R^4$ is formed by addition to the vinyl groups of initial Gp products. Thus, $R^4$ can be any substituent consistent with that formed by a facile addition reaction. Thus, both added substituents can be, for example, OH or halo, and these substituents can be further substituted, or the addition reagent may be of the form HX wherein H is added to the ring-adjacent carbon to provide $R^4$ of the form $$\begin{array}{c} -CH_2CH_3. \\ | \\ X \end{array}$$

The vinyl group can also be oxidized to obtain $R^4$ as $CH_2OH$, —CHO, or COOH and its salts and esters.

Thus, in general $R^4$ represents any substituents to which the vinyl group —CH=CH$_2$ is readily converted by cleavage or addition, and further resultants of reaction of leaving groups with additional moieties. Typical $R^4$ substituents include:

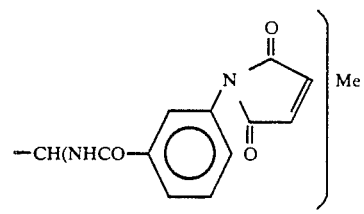

—CH(imidazole)Me,

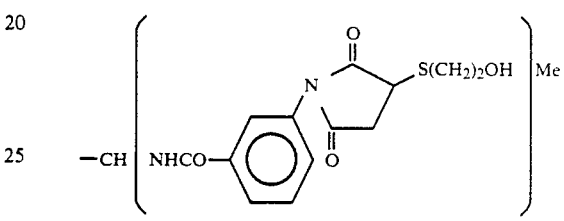

CH(OH)Me, —CHBrMe, —CH(OMe)Me, —CH(pyridinum bromide)Me, —CH(SH)Me and the disulfide thereof, —CHOHCH$_2$OH, —CHO, and —COOH or —COOMe.

When $R^4$ is —L—P, the substituent formula "—L—P" represents a substituent wherein —L— is selected the group consisting of

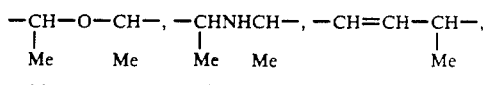

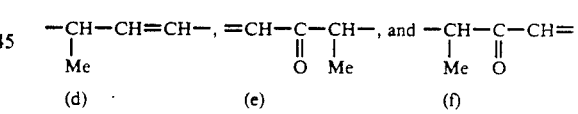

and P is selected from the group consisting of Gp wherein Gp is of the formula 1-6 shown in FIG. 1, but lacking $R^4$ and conjugated through the position shown in FIG. 1 as occupied by $R^4$ to L, and a porphyrin of the formula

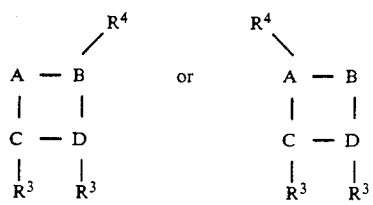

wherein $R^3$ and $R^4$ are as above-defined, and the unoccupied bond is then conjugated to L. It is understood that the abbreviation

represents a porphyrin of the formula:

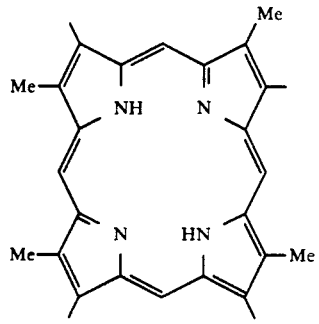

(It is also understood that when —L— is of the formula (e) or (f), the ring system to which the double bond is attached will have a resonance system corresponding to

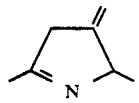

in the ring to which the double bond is attached, as shown.)

Typical embodiments of —L—P include

—CH=CHCH—BPD;  (formula 3)
   |
   Me

—CH=CHCH—BPD;  (formula 4)
   |
   Me

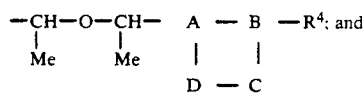

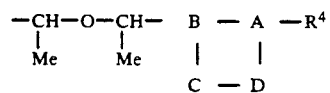

wherein $R^4$ is as above defined. Thus, compounds of the invention include:

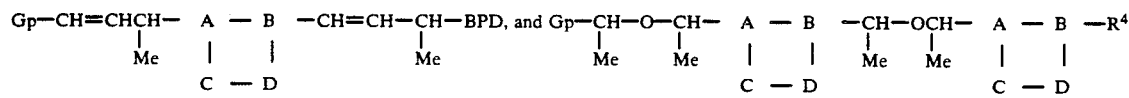

and the like.

The dimers and oligomeric compounds of the invention can be prepared using reactions analogous to those for dimerization and oligomerization of porphyrins per se. The green porphyrins or green porphyrin/porphyrin linkages can be made directly, or porphyrins may be conjugated, flowed by a Diels-Alder reaction of either or both terminal porphyrins to convert to the corresponding green porphyrin.

For formation of compounds of the invention where —L— is of the formula

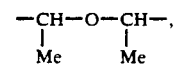

i.e., an ether linkage, the Gp vinyl group is converted to the halide, preferably the chloride, by treating the Gp or prophyrin in a solution of, for example, methylene chloride with HBr to recover the addition product. The resulting product is harvested by evaporation in vacuo, redissolved in methylene chloride and added to an insoluble base such as solid potassium carbonate. To this is added an equivalent of the tetrapyrrole-type nucleus "P" to be linked wherein the reactive $R^4$ moiety of "P" is 1-hydroxyethyl. The mixture is stirred for the appropriate amount of time, around 12 hours, generally, and the resulting diastereomeric pair of dimers (the enantiomeric paired form and a meso form) can be separated from the mixture chromatographically. The tetrapyrrole-type nucleus represented by "P" in this procedure can be either another Gp or a porphyrin.

If the "P" substitutent is a porphyrin, an additional vinyl group may be made available for further halogenation and further reaction to form higher order oligomers.

For embodiments wherein —L— contains a vinyl group, the dimers are obtained by treating Gp or porphyrin wherein $R^4$ is 1-hydroxyethyl with an equivalent amount of the linking tetrapyrrole-type nucleus also having the linking $R^4$ as 1-hydroxyethyl with a strong, non-nucleophilic acid, such as trifluoromethyl sulfonic acid. This treatment results in precipitation of the resulting methylpropenyl linked dimer. (The ether-linked dimer can be formed as a side product in this reaction by substituting alternate acids such as sulfuric acid.)

The amino-linked compounds can be formed by treatment of the vinyl group with HBr followed by treatment with the appropriate amine to obtain the desired linkage.

The Gp used in the methods of the invention can also be conjugated to additional components which supplement its efficacy, depending on the application. If used in purging of malignant cells in bone marrow, the Gp can be further conjugated to, or used in conjunction with, additional cytotoxic agents which are either cytotoxic per se or are activated by light. For example, the Gp of the invention could be conjugated to protein toxins such as diphtheria toxin, ricin A, Pseudomonas toxin, or to nonproteinaceous toxins. In this embodiment, the homing capacity inherent in the Gp is used to direct the additional cytotoxic components preferentially to the malignant cells.

Alternatively, in either the purging or diagnostic application, the homing capacity of the Gp can also be enhanced by conjugation to a moiety which is specific for malignant, as opposed to normal, cells. This target-specific component can be, for example, an immunoglobulin or portion thereof or a ligand specific for receptor.

The immunoglobulin component can be any of a variety of materials. It may be derived from polyclonal or monoclonal antibody preparations and may contain whole antibodies or immunologically reactive fragments of these antibodies such as F(ab')₂, Fab, or Fab' fragments. Use of such immunologically reactive fragments as substitutes for whole antibodies is well known in the art. See, for example Spiegelberg, H. L., in "Immunoassays in the Clinical Laboratory" (1978) 3:1-23.

Polyclonal anti-sera are prepared in conventional ways by injecting a suitable mammal with antigen to which antibody is desired, assaying the antibody level in serum against the antigen, and preparing anti-sera when the titers are high. Monoclonal antibody preparations may also be prepared conventionally such as by the method of Koehler and Milstein using peripheral blood lymphocytes or spleen cells from immunized animals and immortalizing these cells either by viral infection, by fusion with myleomas, or by other conventional procedures, and screening for production of the desired antibodies by isolated colonies. Formation of the fragments from either monoclonal or polyclonal preparations is effected by conventional means as described by Spiegelberg, H. L., supra.

Particularly useful antibodies for the methods herein include the monoclonal antibody preparation CAMAL-1 which can be prepared as described by Malcolm, A., et al, *Ex Hematol* (1984) 12:539-547; CAMAL is a tumor marker.

A ligand specific for receptor refers to a moiety which binds a receptor at the malignant cell surface, and thus contains contours and charge patterns which are complementary to those of the receptors. It is well understood that a wide variety of cell types have specific receptors designed to bind hormones, growth factors, or neurotransmitters. Some of these are present on certain types of malignant cells. However, while these embodiments of ligands specific for receptor are known and understood, the phrase "ligand specific for receptor", as used herein, refers to any substance, natural or synthetic, which binds specifically to a receptor.

The conjugation of the target-cell-specific component or cytotoxic component to the Gp can be effected by any convenient means. For proteins, such as Ig and peptide-type ligands, a direct covalent bond between these moieties may be effected, for example, using a dehydrating agent such as a carbodiimide. A particularly preferred method of covalently binding Gp to the immunoglobulin moiety is treatment with 1-ethyl-3-(3-dimethylamino propyl) carbodiimide (EDCI) in the presence of a reaction medium consisting essentially of dimethyl sulfoxide (DMSO). Other dehydrating agents such as dicyclohexylcarbodiimde or diethylcarbodiimide could also be used as well as conventional aqueous and partially aqueous media.

Nonprotein receptor ligands can be conjugated to the Gp according to their relevant functional groups by means known in the art.

The active moieties of the conjugate may also be conjugated through linker compounds which are bi-functional, and are capable of covalently binding each of the two active components. A large variety of these linkers is commercially available, and a typical list would include those found, for example, in the catalog of the Pierce Chemical Co. These linkers are either homo or heterobifunctional moieties and include functionalities capable of forming disulfides, amides, hydrazones, and a wide variety of other linkages.

Other linkers include polymers such as polyamines, polyethers, polyamine alcohols, derivatized to the components by means of ketones, acids, aldehydes, isocyanates, or a variety of other groups.

The techniques employed in conjugating the active moieties of the conjugate include any standard means and the method for conjugation does not form part of the invention. Therefore, any effective technique known in the art to produce such conjugates may be used.

For use in the method of the invention either the green porphyrin compounds per se or the conjugates may be further derivatized to a compound or ion which additionally labels the Gp. A wide variety of labelling moieties can be used, including radiosotopes, chromophores, and fluorescent labels.

The compounds which are Gp alone or are conjugates of Gp with a specific binding substance can be labeled with radioisotopes by coordination of a suitable radioactive cation in the porphyrin system. Useful cations include technetium, gallium, and indium. In the conjugates, either or both the specific binding substances can be linked to or associated with label, or the label can be conjugated or coordinated with the Gp moiety itself.

Gp or its conjugates can be used as described or when complexed to appropriate metal ions. As is generally understood in the art, the tetrapyrrole-type nucleus can be treated with an appropriate ion such as magnesium ion, zinc, ion, stannous ion, and the like to obtain the metal complex. As stated above, the metal ion may also be a radiolabel. The nature and desirability of the inclusion of a metal ion in the tetrapyrrole-type nucleus depends on the specific application for which the compound is intended. When the inclusion of a metal ion is desired, the desired metal ion can be inserted using the appropriate metal salts under known conditions. For example, zinc ion can be introduced by treating the compound with zinc acetate in 1:1 methylene chloride:-methanol.

Methods of Purging Malignant Cells

The bone marrow to be purged is removed from the subject using standard techniques and mononuclear cells are used in the purging protocol. While bone marrow is the most commonly used source of hemopoietic cells for transplants, other sources, of such cells, such as blood, could also be used.

The foregoing Gp compounds and/or conjugates, and in particular the BPD forms thereof, are used in the method of the invention by contacting the hemopoietic cells of the bone marrow to be purged with the selected Gp or a mixture of these Gps in an amount and for a time effective to cause the uptake of the Gp composition by malignant cells. Excess Gp composition is then removed by standard washing procedures. The resulting composition containing malignant cells which are now effectively labeled by the Gp composition is then irradiated with a light source emitting radiation in the range absorbed by the Gp composition used, typically in the range 670-780 nm, for a time effective to cause the destruction of the malignant cells.

The concentrations of Gp used to contact the cells of the marrow are dependent on the specific Gp component or components chosen, but, for example, for the BPD compounds illustrated in FIG. 2 typical concentrations are in the range of 5-100 ng$10^6$ cells/ml, preferably 10-20 ng/$10^6$ cells/ml under serum-free conditions. At these preferred concentrations, malignant cells are destroyed upon irradiation while growth of normal myeloid progenitors is enhanced. The time of incubation also is dependent on the choice of photoactivator Gp, but for the illustrated BPD compounds of FIG. 2, suitable times are in the range of 30 minutes to 1 hour.

Irradiation of the treated marrow is typically 1-2 hours with an intensity of about 5-6 J/cm$^2$, preferably 5.4 J/cm$^2$. Useful light sources include both laser (690 nm) and nonlaser (visible spectrum) systems.

The nonlaser light sources include high-intensity discharge lamps (e.g., mercury vapor, metal halide, high pressure sodium), short arc discharge lamps (e.g., xenon, tin halide, compact source iodide), normal incandescent or quartz halogen incandescent, and fluorescent lamps.

Optimum conditions for incubation, removal of excess Gp, and irradiation can readily be ascertained by generally known techniques.

By way of further illustration, in preparing autologous bone marrow for a transplantation procedure in patients, the following typical protocol is followed:

Bone marrow (BM) cells are removed under operating room conditions from the patient. The BM cells are separated (for example, by density centrifugation) to obtain a population of mononuclear cells. This cell population will contain normal hemopoietic cells (required to reconstitute the patient's hemopoietic system followed autologous BM transplantation) but may also contain a variable number of malignant cells. The BM cells are washed and diluted to an appropriate concentration for treatment (5 × $10^7$-$10^8$ cells/ml) in transparent containers. Benzoporphyrin derivative (BPD) is diluted from frozen stock solution and added at the appropriate concentration to the BM cells. The BM cells are incubated with the BPD in the dark for approximately 1-2 hours. The cells are then centrifuged, the supernatant containing excess BPD decanted, and the cells resuspended in phenol red-free medium containing 10% FCS. The transparent containers are then exposed to visible light for 1-2 hours at room temperature (20° C.) with gentle agitation.

Following light exposure, the BM cells are washed in tissue culture medium and a sample is removed for analysis. The ex vivo purging procedure (BPD+light) causes preferential killing of malignant cells contained in the BM, while leaving adequate numbers of normal cells required for reconstitution of hemopoiesis in the treated patient.

The purged BM cells are cryopreserved until required for autologous BM transplantation. At that time, the cells are thawed and infused intravenously into the patient, who has previously received appropriate ablative therapy to eradicate malignant cells present within the body. These purged autologous BM cells will repopulate the patient's bone marrow such that normal hemopoiesis will result.

The above protocol may be supplemented by additional treatments which enhance or otherwise positively affect the removal of malignant cells while maintaining the capability of the bone marrow to maintain homopoiesis. For example, after treatment with Gp, irradiation, and removal of malignant cells, the remaining portions of the bone marrow can be treated with suitable growth factors to encourage the growth of normal cells. Such factors include, for example, factors derived from various hematopoietic cells.

Assessment of Marrow for Malignant Cells

To ascertain that purging is complete or to evaluate homopoietic cell compositions, such as those from marrow samples in general, the composition which has been treated with Gp is subjected to excitation by light of shorter wavelengths, of the order of 400-490 nm or with UV light, and the presence or absence of typical fluorescence due to the accumulation of the Gp in malignant cells is noted.

This procedure can be conducted either in vivo or ex vivo. The treated cells obtained from bone marrow are treated for a sufficient time to effect the removal of the previously administered Gp, and then again contacted with an effective amount of Gp, in the concentrations generally set forth above, and irradiated with short wavelength light corresponding to the excitation frequency for the Gp used. Fluorescence is detected using standard methods. In addition, the absence of malignant cells which specifically absorb the Gp can be verified by cell-sorting techniques, and the absence of stained malignant cells thus demonstrated.

Thus, the Gp compounds of the invention are useful both for the active removal of malignant cells from the autologous marrow preparations and for evaluation of marrow, e.g., for confirmation that the removal procedure has been successful.

Of course, it is not necessary that the verification procedure utilize the Gp/fluorescence techniques. Any suitable method for detecting the presence or absence of malignant cells can conveniently be used.

The following examples demonstrate the efficacy of the invention approach, and illustrate the method of the invention.

EXAMPLE 1

Differential Uptake of BPD by Leukemic Cells

Preparation of Cells

The following leukemic cell lines were used for analysis:

L1210 (a murine lymphocytic leukemia cell line);
HL60 (a human acute promyelocytic leukemia cell line); and
K562 (a human chronic myelogenous leukemia cell line).

These lines were maintained in phenol red-free DME (Dulbecco's Modified Eagle's) medium supplemented with 10% fetal calf serum (FCS) in a 10% CO$_2$ incubator at 37° C. and split according to ATCC specifications.

Mononuclear cells were extracted from both leukemic clinical isolates and normal human bone marrow and peripheral blood (collected in heparinized tubes) via Ficoll-Hypaque density gradient centrifugation. For blood samples, whole blood was diluted by a factor of 2 in PBS followed by layering of 10 ml of diluted blood over 3 ml Ficoll-Hypaque. After 17 minutes of centrifugation at 1500 rpm, the mononuclear band containing all mononuclear white blood cells was removed. These cells were washed three times in PBS and used directly or stored in DME medium containing 10% DMSO at low temperature. The cyropreserved cells were used after quick warming in 37° C. water bath, rinsing in ethanol and dilution by a factor of 10 in PBS followed by washing three times in PBS to remove DMSO.

Bone marrow was extracted from the femur and tibia of 6–8 week old DBA/2J female mice by flushing and aspiration with a 25 gauge needle to form a single cell suspension. The bone marrow cells were centrifuged and washed in sterile PBS and viability counts performed.

Mouse spleen cells were obtained by extraction from the same DBA/2J mice and passed through a wire mesh to create a single cell suspension. These cells were used directly or cryopreserved as described above.

General Procedure

Before FACS analysis, all cells were incubated in a 10% $CO_2$, 37° C. incubator with the BPD or a marking dye as described below for 30 minutes in a phenol red-free DME medium in the absence of FCS unless otherwise indicated. Cells were then washed in PBS to remove excess photosensitizer, centrifuged at 1100 rpm and resuspended in phenol red-free medium and FACS performed.

The Photoactivator

Figures 1, 2, 3:
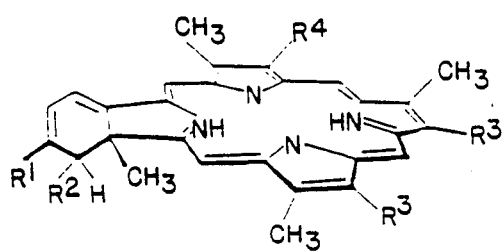

Preliminary spectrofluorometric data showed that BPD-DA, as shown in FIG. 2, is excited by 420 nm and to a lesser extent by 356 nm (UV) light. This compound fluoresces at 690 nm. Further preliminary data with regard to all four forms of BPD shown in FIG. 2 were obtained by incubating HL60 cells with 5, 10 or 20 $\mu$g/ml of each of these compounds for 30 minutes and measuring the fluorescence emitted after UV or visible (488 nm) light excitation. When sorted by FACS, it appears, as shown in FIG. 3, that BPD-MA showed maximal fluorescence. Accordingly, BPD-MA was used in the subsequent analyses.

Specificity for Leukemic Cells

Correlation of absorption of BPD-MA with the leukemic nature of the cells was confirmed by treatment with 3,5-dioctadecyloxacarbocyanine perchlorate (DiO) a cationic lipophilic probe which emits green fluorescence when excited by 489 nm light. The dye does not transfer from cell to cell. Normal mouse bone marrow or spleen cells incubated with 10 $\mu$g/ml BPD-MA were mixed immediately before application of FACS with L1210 cells incubated for the same time with 10 $\mu$g/ml BPD-MA and 100 $\mu$g/ml DiO.

Figures 1, 2, 3, 4:
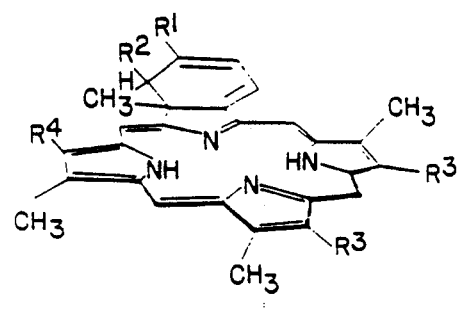

The cells were sorted into 10 fractions by application of FACS performed using UV excitation and red fluorescence as a criterion in response to the absorbed BPD-MA. Each fraction was then reanalyzed for the green fluorescence of DiO using 488 nm excitation and a 530 nm filter; the presence of L1210 cells in each fraction could thereby be determined. These results are shown in FIG. 4. Fraction 10, which had the highest red fluorescence due to the presence of BPD, also contained the highest proportion of green fluorescence. Thus, the presence of BPD correlates with the presence of L1210 cells. Cytospins of fraction 1 and fraction 10 showed that the majority of cells in fraction 10 fluoresce green while no cells in fraction 1 exhibited green fluorescence upon blue light excitation and examination in a fluorescent microscope. Thus, the high red-fluorescing BPD-containing cells of fraction 10 are identified as the L1210 cells.

Figures 1, 2, 3, 4, 5:
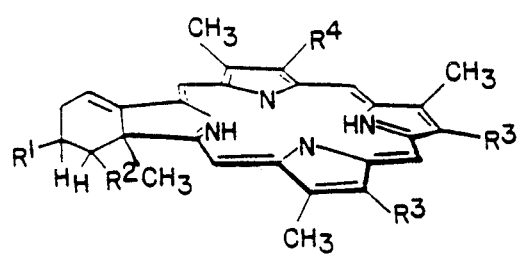
Figures 1, 2, 3, 4, 5, 6:
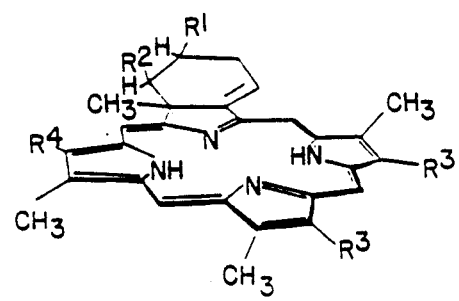
Figures 1, 2:
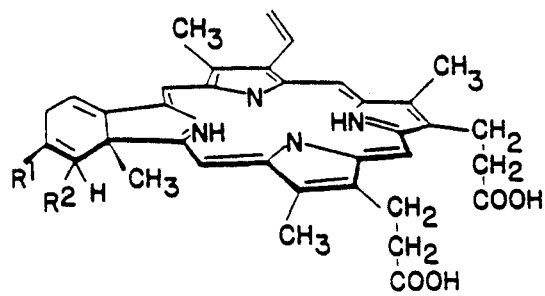
Figure 2:
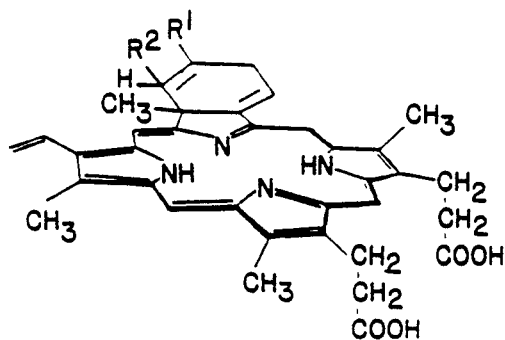
Figures 2, 3:
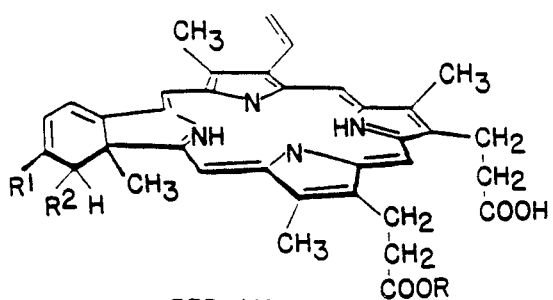
Figures 2, 3, 4:
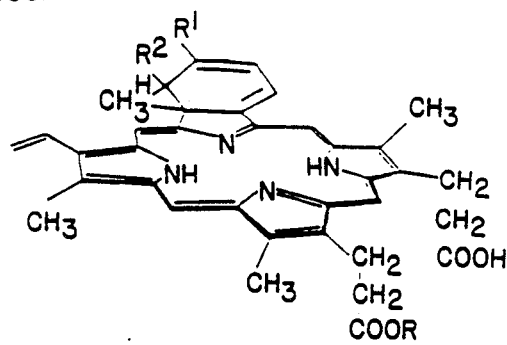
Figure 3A:
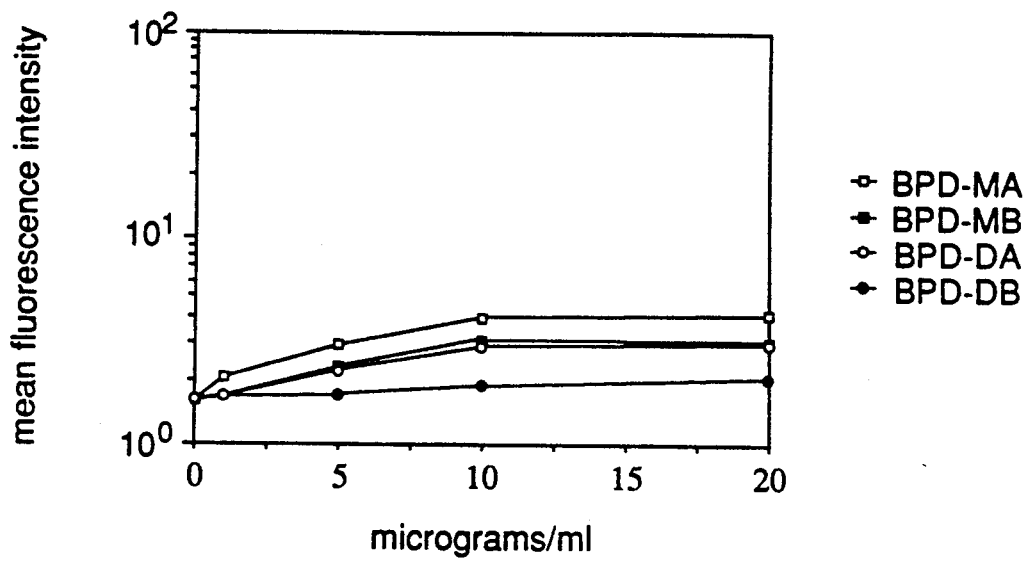
FIGS. 3A and 3B show the uptake of BPD by leukemic HL60 cells.
Figure 3B:
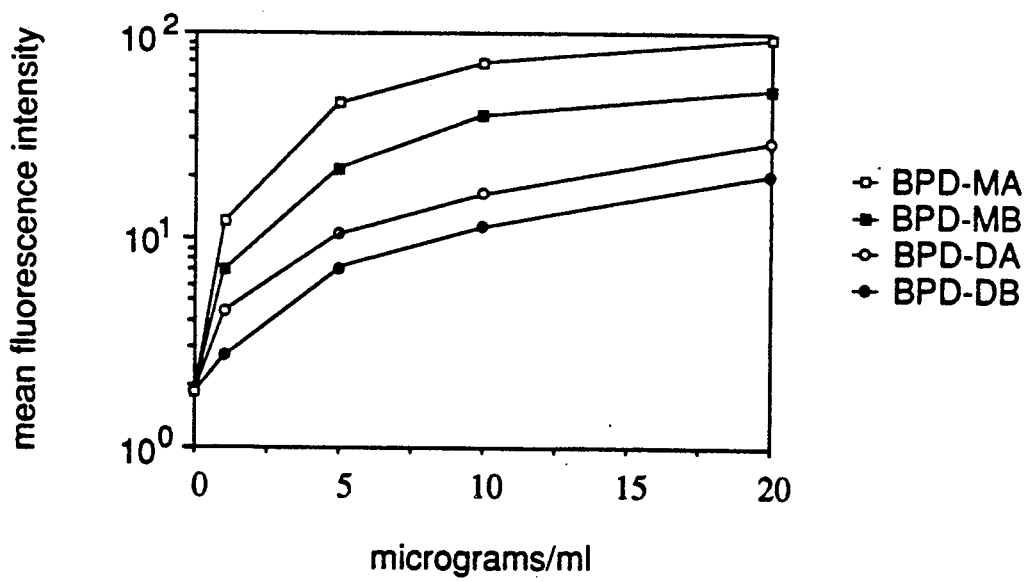
Figure 4:
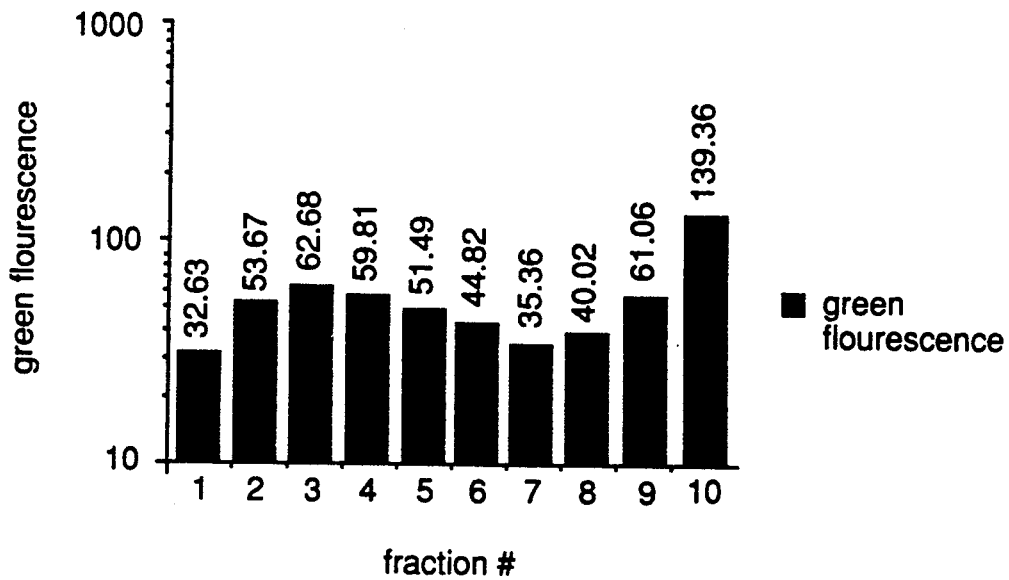
Figure 5:
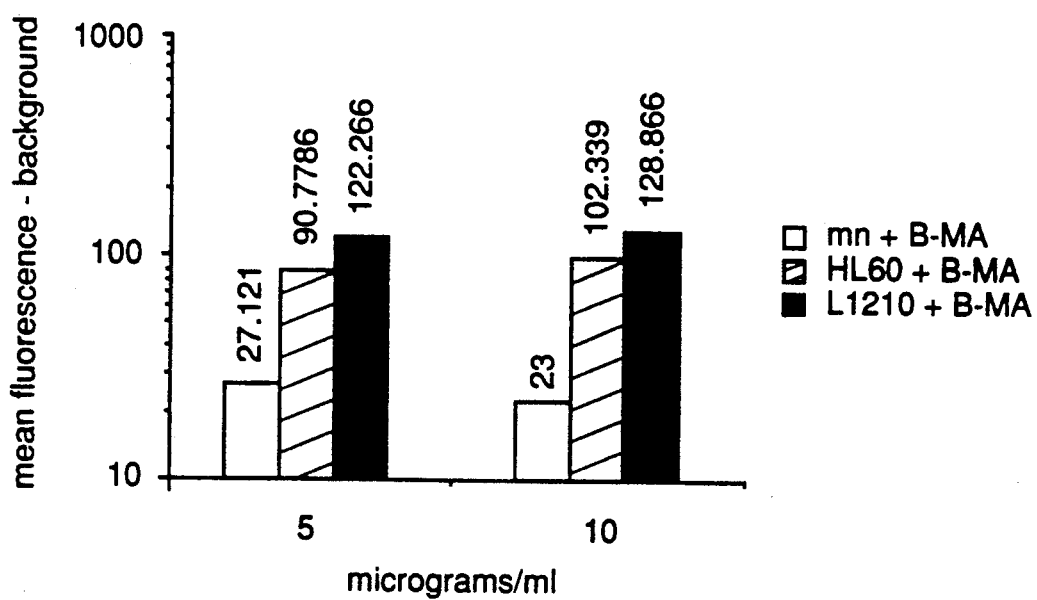
Figure 6:
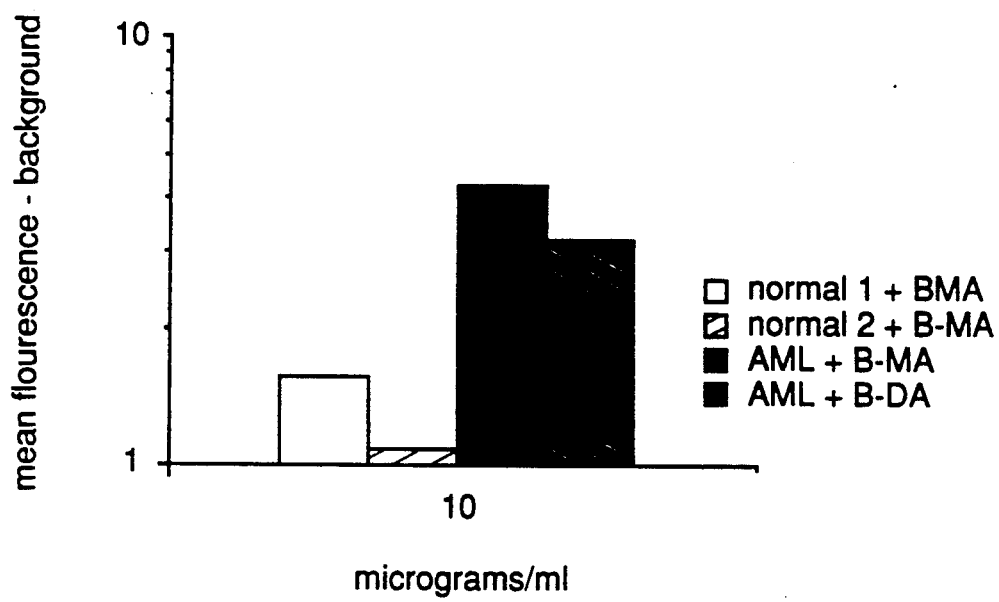
Figure 7:
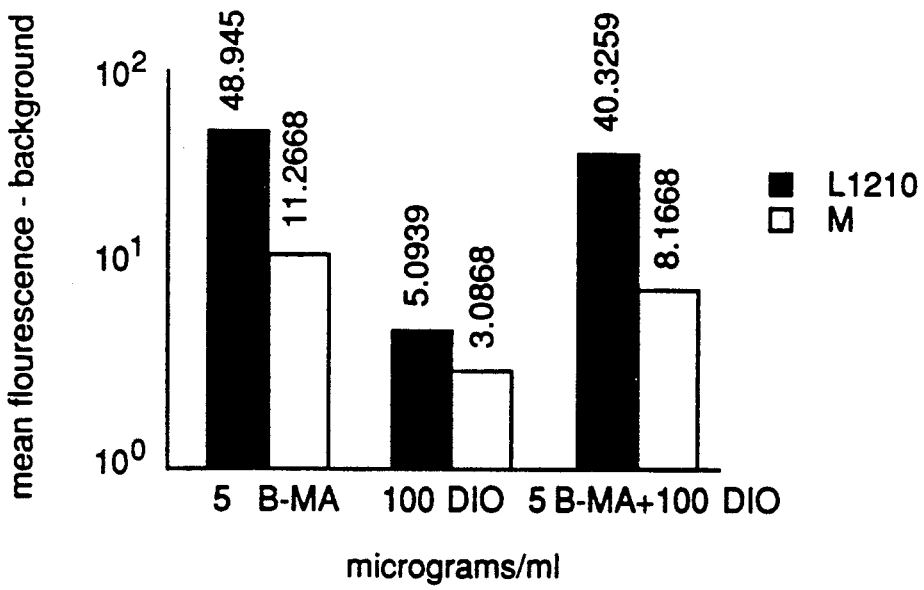

FACS analysis based on red fluorescence due to absorbed BPD-MA consistently showed higher levels of fluorescence with respect to the leukemic cell fraction. FIG. 5 shows the results obtained when normal human bone marrow or peripheral blood mononuclear cells were incubated in BPD-MA for 30 minutes as compared with analogous incubation of K562 or L1210 cells. Similarly, FIG. 6 shows the results of analysis of normal human bone marrow cells as compared to a clinical isolate of AML cells. In both cases, uptake with regard to the leukemic cells is demonstrably greater. Similar results are obtained for the murine leukemic cell line L1210 as compared to normal mouse spleen cells as shown in FIG. 7.

Figure 8:
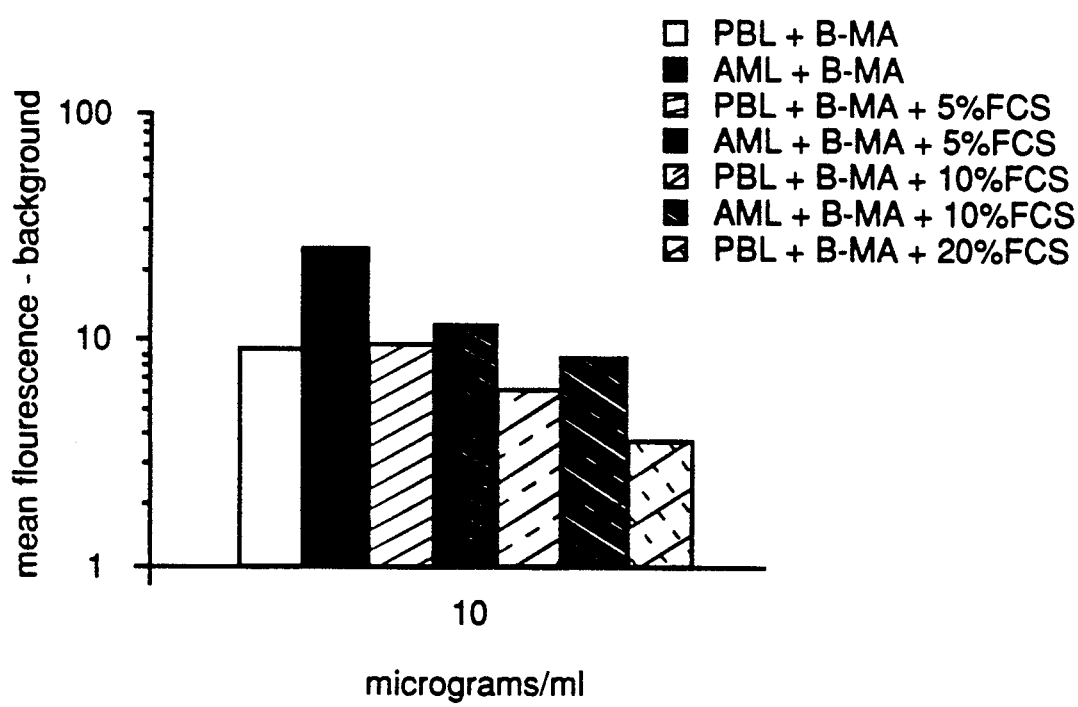
FIG. 8 shows the effect of serum on BPD uptake.

FIG. 8 shows the effect of the presence of fetal calf serum on the uptake of BPD-MA. Cells were incubated with 5 $\mu$g/ml BPD-MA for 30 minutes in the absence of FCS or in the presence of 5, 10 or 20% FCS. Using normal PBL or AML clinical isolates. As shown in FIG. 8, differential uptake is decreased in the presence of increasing amounts of FCS.

EXAMPLE 2

Replacement of Treated

Malignant/Hemopoietic Cell Mixture In Vivo

The results of this example show that normal murine hemopoietic progenitors remain viable and capable of reconstituting hemopoiesis in lethally irradiated DBA/2 mice after irradiation protocols with BPD which eliminate malignant cells from the mixed population. L1210 cells, a typical leukemic cell line used by the National Cancer Institute to test the efficacy of all new chemotherapeutic agents, were used as the malignant cells.

Eight- to ten-week-old DBA/2 female mice were exposed to lethal $\gamma$-irradiation (950 rads) from a cobalt-60 source to destroy the hemopoietic system.

About 1–2 hours post irradiation, the mice were injected intraperitoneally with mixtures of malignant and nonmalignant hemopoietic cells which had been subjected to the invention purging method to ascertain the capability of the mixtures to reconstitute hemopoiesis of the irradiated mice.

Four mice were thus injected with a mixture of $10^6$ spleen cells and $10^6$ L1210 cells, which mixture had been incubated with 100 ng/ml of BPD-MA for 30 min and then exposed to 5.4 J/$cm^2$ of visible light for 40 min. Control groups of two mice each received no spleen cells, or received spleen cells only with no malignant cells.

The treated mice were then placed in cages fitted with nylon filters and monitors for ascites formation and long-term survival. The long-term survival of mice injected with the BPD-treated mixture was similar to that from mice injected with spleen cells only, and significantly higher than that for untreated mice.

EXAMPLE 3

Comparative PDT Sensitivity of

Normal and Leukemic Cells

Mononuclear cells were separated from whole blood or bone marrow collected in heparinized tubes using Ficoll-Hypaque density gradient centrifugation according to standard procedures. Cryopreserved samples were thawed quickly in a 37° C. water bath and washed three times with phosphate-buffered saline to remove residual DMSO. The recovered marrow mononuclear cells were diluted to $1-2\times 10^6$ cells/ml; recovered PBL mononuclear cells were diluted to $2-4\times 10^6$ cells/ml. Cell samples from both normal and malignant subjects were obtained in this way.

The Gp compound, BPD-MA, was diluted from frozen stock of 400 μg/ml in DMSO and added to aliquots of 0.5-1 ml cells in 5 ml polystyrene tubes to give final concentrations of BPD of 0-100 ng/ml. The cells were incubated at 37° C. with 5% $CO_2$ for an hour, centrifuged for 10 min at 1500 rpm, and resuspended in fresh ISCOVES with or without 10% fetal calf serum. The cells were then irradiated using a bank of 4 cool white deluxe fluorescent lights which provide 1.5 mW/cm² for 1 hour at room temperature.

Samples were then plated in duplicate in a standard colony assay which is conducted by plating 0.3 ml cells, 0.3 ml pretested PHA-leucocyte-conditioned media, 0.9 ml fasting human plasma, and 1.4 ml methylcellulose with β-mercaptoethanol.

Colonies were counted after 14 days, and the results were expressed as the number of colonies counted or as a percentage of untreated irradiated controls.

Figure 9A:
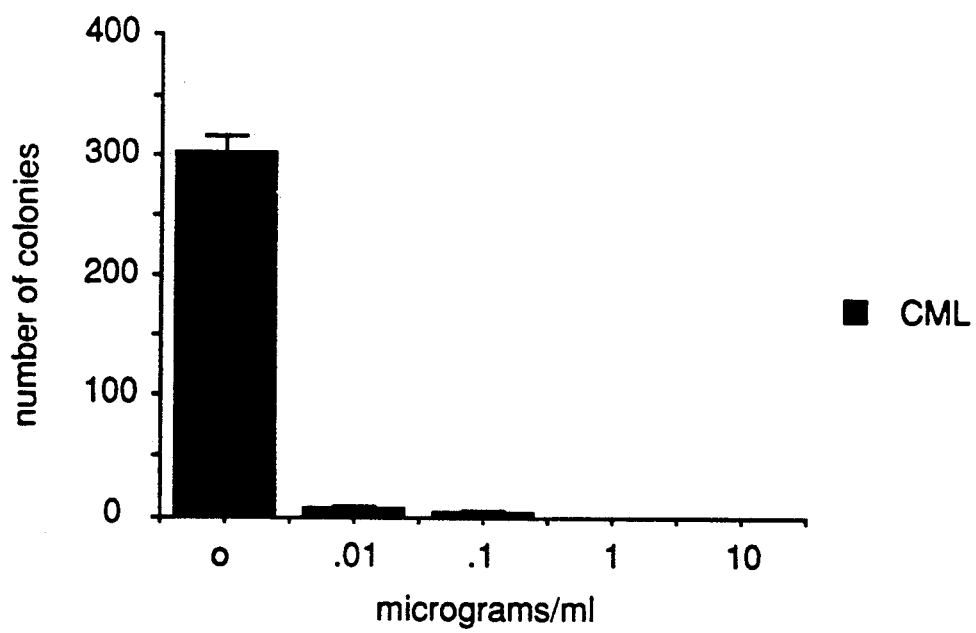
FIGS. 9A and 9B show the effect of BPD concentration on toxicity to malignant cells.
Figure 9B:
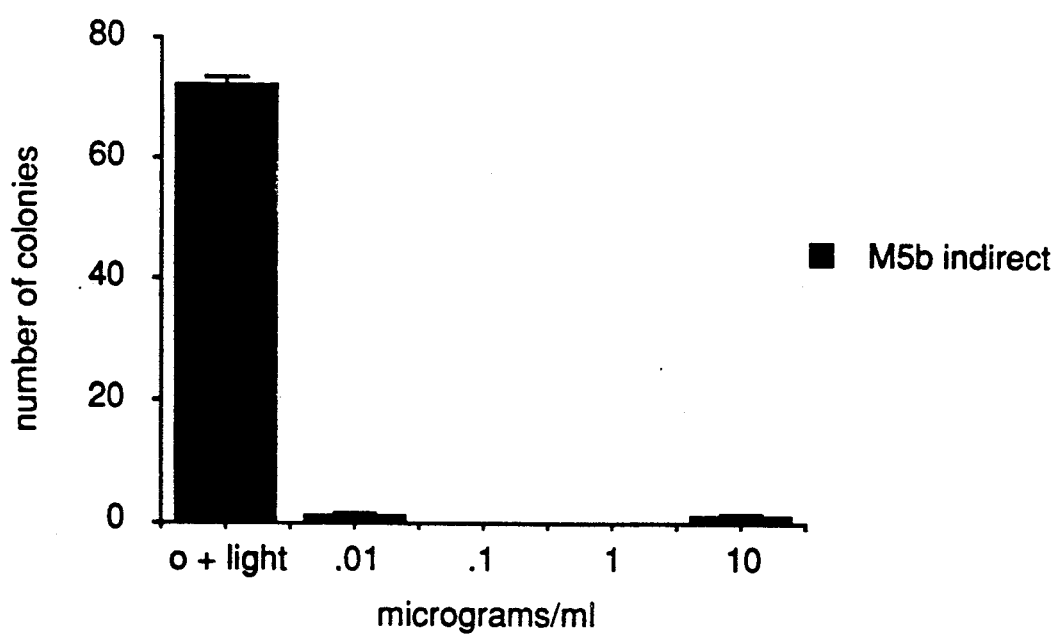
Figure 10A:
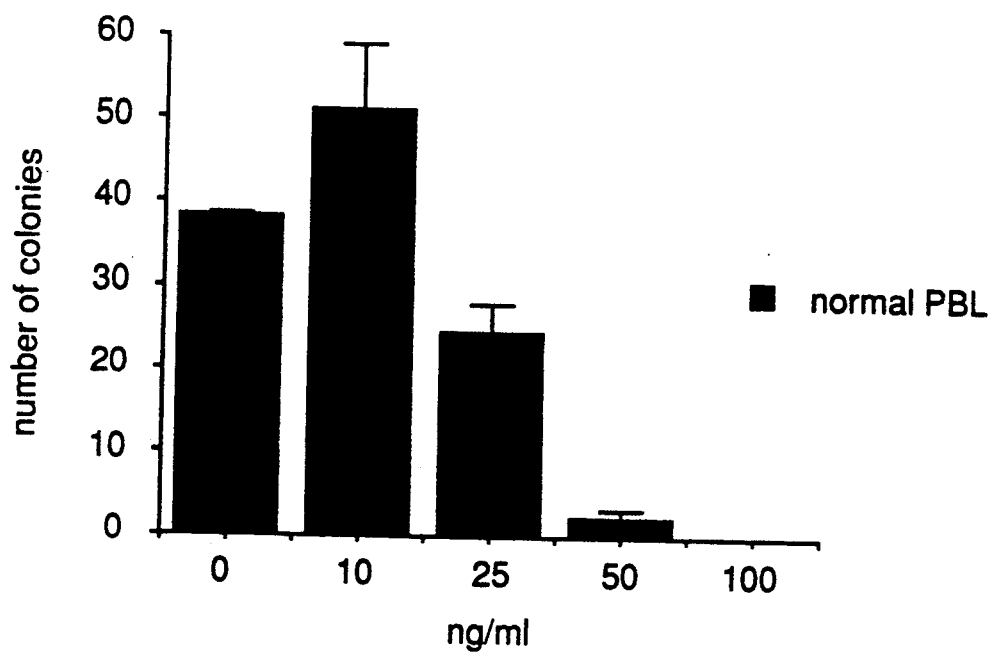
FIGS. 10A and 10B show the effect of BPD concentration on toxicity to wound cells.
Figure 10B:
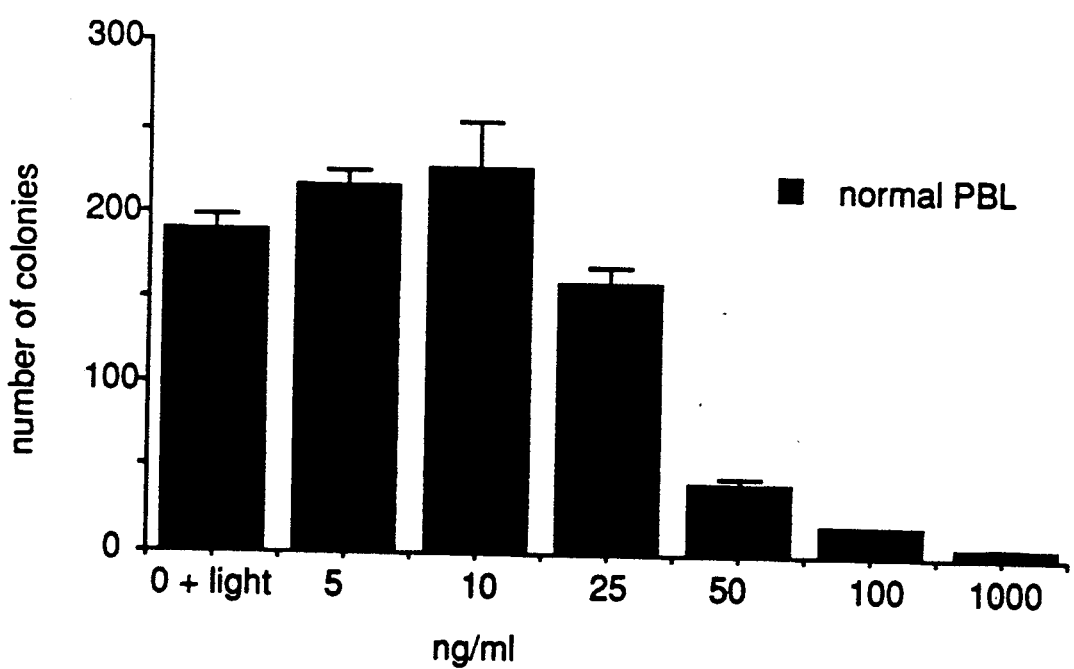

The results of these determinations indicated that an enhanced number of colonies was observed when mononuclear cells from normal bone marrow were subjected to the BPD-MA treatment and irridation protocol, whereas there was a diminution in the number of colonies when bone marrow from patients known to be afflicted with acute myelogenous leukemia or chronic granulocytic leukemia was used. In one determination, using the bone marrow of a patient afflicted with CML, concentrations of BPD-MA as low as 10 ng/ml were capable of virtually extinguishing formation of colonies. These results are shown in FIG. 9A and B. On the other hand, similar concentrations of BPD-MA, when used to treat normal cells, did not cause significant inhibition of colony formation capability up to concentrations of 25 ng/ml (FIGS. 10A and 10B).

We claim:

1. A method to purge a composition of bone marrow cells of malignant cells, which method comprises contacting said cell composition containing malignant cells with a composition of green porphyrin (Gp) for a time sufficient to permit uptake of the Gp by said malignant cells; followed by irradiating said cell composition with light of a wavelength absorbed by said Gp for a time sufficient and with an intensity sufficient to effect the destruction of the malignant cells, wherein said Gp is of the formula

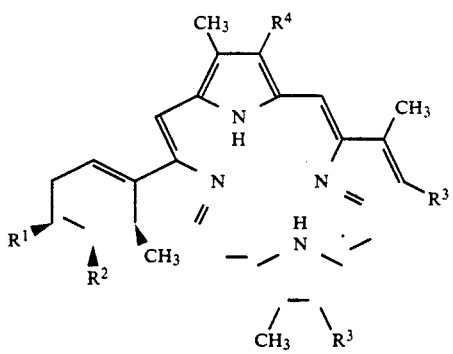

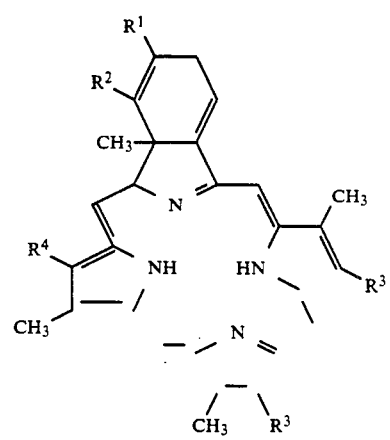

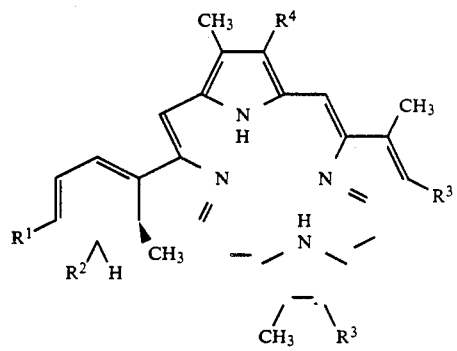

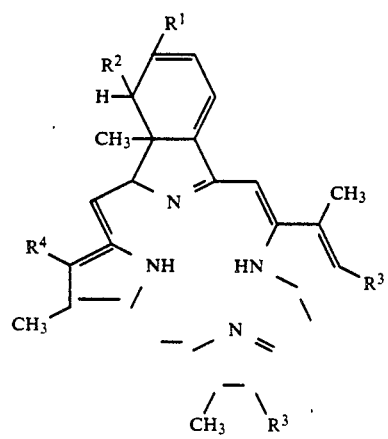

-continued

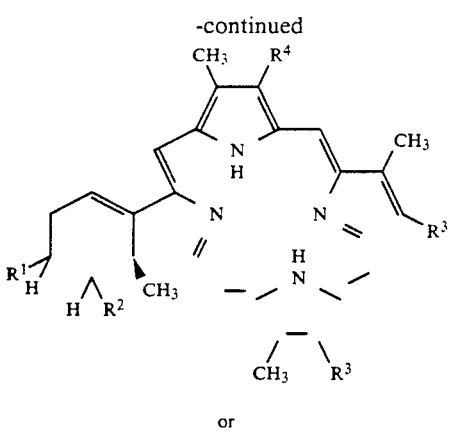

or

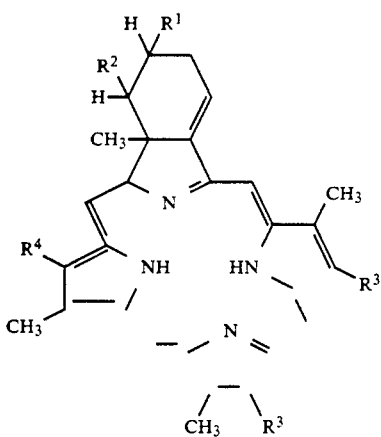

or the metalated and/or labeled form thereof;
wherein each $R^1$ and $R^2$ is independently selected from the group consisting of carbalkoxy (2-6C), alkyl (1-6C) sulfonyl, aryl (6-10C) sulfonyl, aryl (6-10C); cyano; and —CONR$^5$CO— where $R^5$ is aryl (6-10C) or alkyl (1-6C);

each $R^3$ is independently carboxyalkyl (2-6C) or a salt, amide, ester or acylhydrazone thereof, or is alkyl (1-6C); and $R^4$ is CHCH$_2$, —CH$_2$OR$^{4'}$, —CHO, —COOR$^{4'}$, —CH(OR$^{4'}$)CH$_3$, CH(OR$^{4'}$)CH$_2$OR$^{4'}$, —CH(SR$^{4'}$)CH$_3$, —CH(NR$^{4'}{}_2$) CH$_3$, —CH(CN)CH$_3$, —CH(COOR$^{4'}$)CH$_3$, —CH((OOCR$^{4'}$CH$_3$, —CH(halo)CH$_3$, or —CH(halo)CH$_2$(halo), wherein $R^{4'}$ is H or alkyl (1-6C) optionally substituted with a hydrophilic substituent, or wherein $R^4$ consists of 1-3 tetrapyrrole-type nuclei of the formula —L—P wherein —L— is selected from the group consisting of

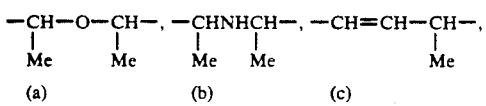

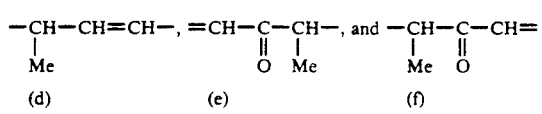

and P is selected from the group consisting of Gp which is of the formula 1-6 but lacking $R^4$ and conjugated through the position shown as occupied by $R^4$ to L, and a porphyrin of the formula:

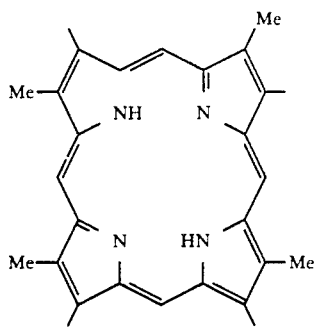

wherein two of the bonds shown as unoccupied on adjacent rings are joined to $R^3$ and one of the remaining bonds shown as unoccupied is joined to $R^4$ and the other to L.

2. The method of claim 1 which further includes removing excess Gp.

3. The method of claim 1 wherein said Gp is of the formula:

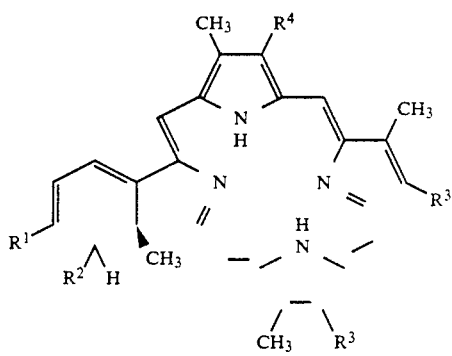

or

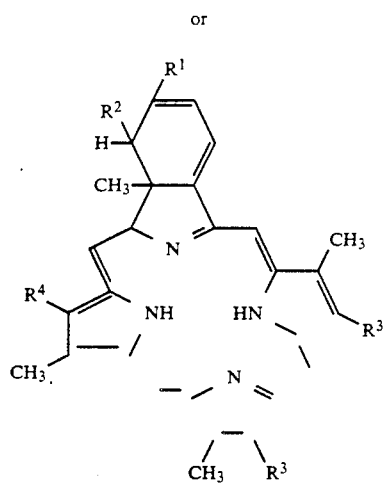

4. The method of claim 3 wherein each $R^3$ is independently carboxyalkyl (2-6C) or a salt, amide, ester or acyl hydrazone thereof.

5. The method of claim 3 wherein each $R^1$ and $R^2$ is independently selected from the group consisting of carbalkoxy (2-6C) and alkyl (1-6C).

6. The method of claim 3 wherein $R^4$ is CHCH$_2$ or CH(OR$^{4'}$) CH$_3$, wherein $R^{4'}$ is H or alkyl (1-6C).

7. The method of claim 4 wherein each $R^3$ is independently carboxyethyl or a salt, amide, or ester thereof.

8. The method of claim 5 wherein each $R^1$ and $R^2$ is independently methoxycarbonyl or ethoxycarbonyl.

9. The method of claim 7 wherein at least one $R^3$ is carboxyethyl or a salt thereof.

10. The method of claim 6 wherein $R^4$ is $CHCH_2$.

11. The method of claim 9 wherein $R^4$ is $CHCH_2$.

12. The method of claim 11 wherein each $R^1$ and $R^2$ is independently methoxycarbonyl or ethoxycarbonyl.

13. The method of claim 1 wherein said Gp is conjugated to a cytotoxic agent.

14. The method of claim 1 wherein said Gp is conjugated to a target-specific moiety specific for said malignant cells.

15. The method of claim 1 wherein said contacting further includes contacting said cell composition with additional chemotherapeutic agents.

16. The method of claim 1 which further includes contacting said cell composition with one or more growth factors.

17. The method of claim 1 wherein said malignant cells are infected with HIV.

18. The method of claim 1 wherein said cell composition is derived from bone marrow.

19. A method to detect the presence or absence of malignant cells in a composition selected from the group consisting of bone marrow and a preparation of cells therefrom, which method comprises contacting said composition with Gp for a time sufficient to effect the uptake of said Gp by malignant cells; followed by irradiating said composition with light at a wavelength effective to excite fluorescence of said Gp; and detecting the presence or absence of said fluorescence wherein said Gp is of the formula

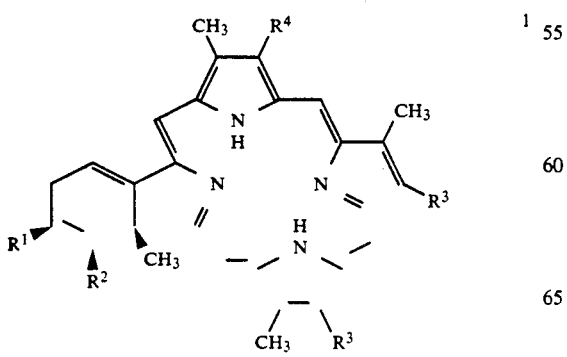

-continued

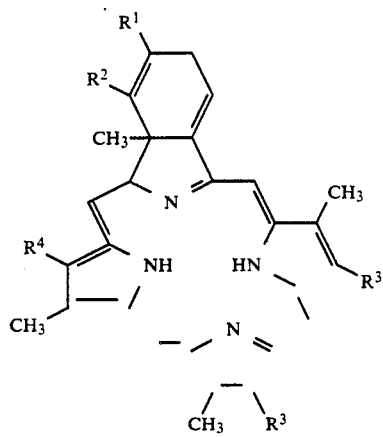

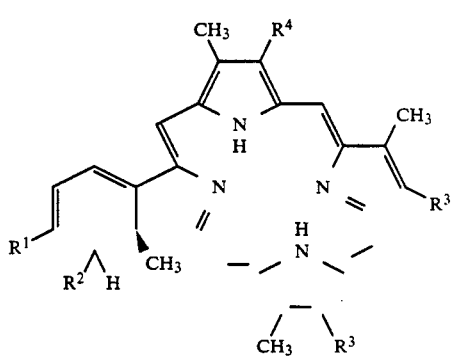

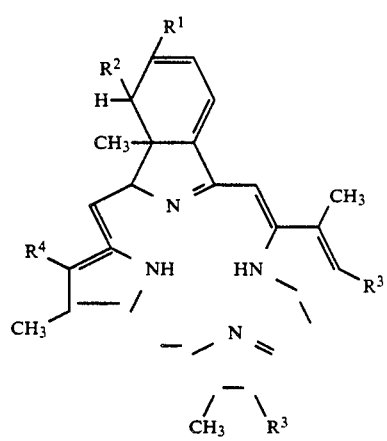

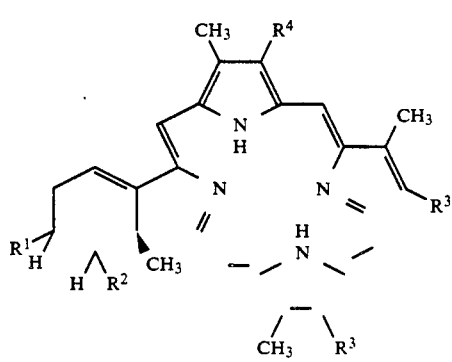

or

-continued

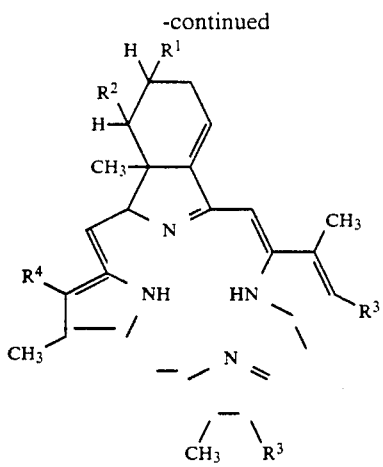

or the metalated and/or labeled form thereof;
wherein each R¹ and R² is independently selected from the group consisting of carbalkoxy (2-6C), alkyl (1-6C) sulfonyl, aryl (6-10C) sulfonyl, aryl (6-10C); cyano; and —CONR⁵CO— where R⁵ is aryl (6-10C) or alkyl (1-6C);

each R³ is independently carboxyalkyl (2-6C) or a salt, amide, ester or acylhydrazone thereof, or is alkyl (1-6C); and R⁴ is CHCH₂, —CH₂OR⁴', —CHO, —COOR⁴', —CH(OR⁴')CH₃, CH(OR⁴')CH₂OR⁴', —CH(SR⁴')CH₃, —CH(NR⁴'₂) CH₃, —CH(CN)CH₃, —CH(COOR⁴')CH₃, —CH((OOCR⁴')CH₃, —CH(halo)CH₃, or —CH(halo)CH₂(halo), wherein R⁴' is H or alkyl (1-6C) optionally substituted with a hydrophilic substituent, or wherein R⁴ consists of 1-3 tetrapyrrole-type nuclei of the formula —L—P wherein —L— is selected from the group consisting of

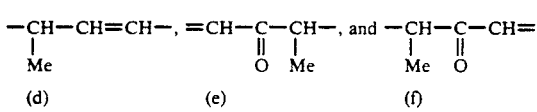

and P is selected from the group consisting of Gp which is of the formula 1-6 but lacking R⁴ and conjugated through the position shown as occupied by R⁴ to L, and a porphyrin of the formula:

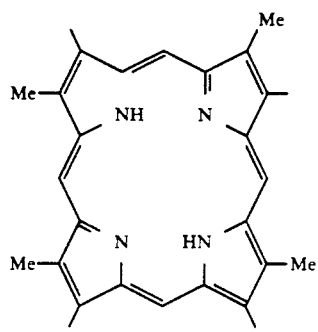

wherein two of the bonds shown as unoccupied on adjacent rings are joined to R³ and one of the remaining bonds shown as unoccupied is joined to R⁴ and the other to L.

20. The method of claim 19 which further includes removal of excess Gp.

21. The method of claim 19 wherein said Gp is of the formula:

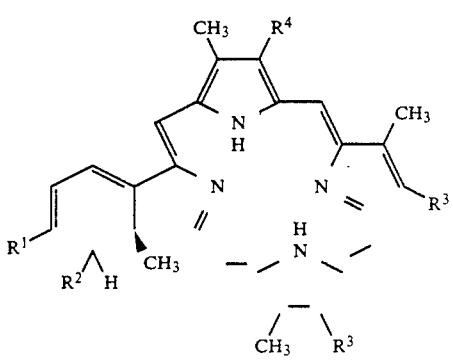

or

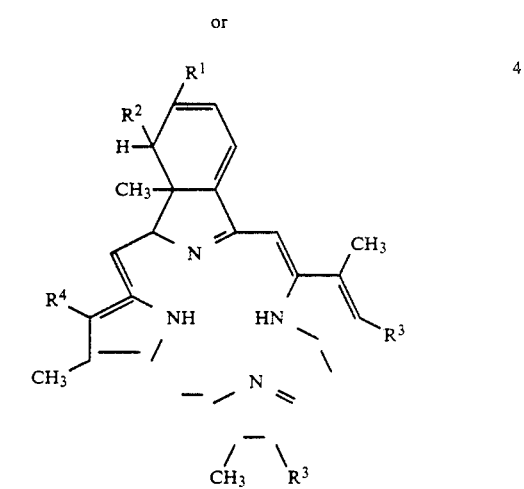

22. The method of claim 21 wherein each R³ is independently carboxyalkyl (2-6C) or a salt, amide, ester or acyl hydrazone thereof.

23. The method of claim 21 wherein each R¹ and R² is independently selected from the group consisting of carbalkoxy (2-6C) and alkyl (1-6C).

24. The method of claim 21 wherein R⁴ is CHCH₂ or CH(OR⁴')CH₃, wherein R⁴' is H or alkyl (1-6C).

25. The method of claim 22 wherein each R³ is independently carboxyethyl or a salt, amide, or ester thereof.

26. The method of claim 23 wherein each R¹ and R² is independently methoxycarbonyl or ethoxycarbonyl.

27. The method of claim 25 wherein at least one R³ is carboxyethyl or a salt thereof.

28. The method of claim 24 wherein R⁴ is CHCH₂.

29. The method of claim 27 wherein R⁴ is CHCH₂.

30. The method of claim 29 wherein each R¹ and R² is independently methoxycarbonyl or ethoxycarbonyl.

31. The method of claim 19 wherein said Gp is conjugated to a homing moiety specific for said malignant cells.

32. The method of claim 19 wherein said malignant cells are infected with HIV.

33. A method to treat a patient afflicted with a blood or bone marrow malignancy, which method comprises:
removing bone marrow from said patient;
recovering the mononuclear cells from the marrow;
purging said cells of malignant cells according to the method of claim 1; and
returning said treated bone marrow cells to said patient.

34. The method of claim 33 wherein said patient has been treated to destroy all bone marrow and blood cells prior to said returning step.

35. The method of claim 19 wherein said composition is bone marrow.

36. A method to purge a composition of bone marrow cells of malignant cells, which method comprises contacting said cell composition containing malignant cells with a composition of green porphyrin (Gp) for a time sufficient to permit uptake of the Gp by said malignant cells; followed by
irradiating said cell composition with light of a wavelength absorbed by said Gp for a time sufficient and with an intensity sufficient to effect the destruction of the malignant cells,
wherein said Gp is of the formula

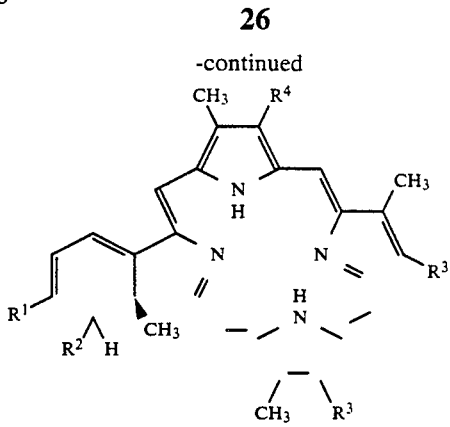

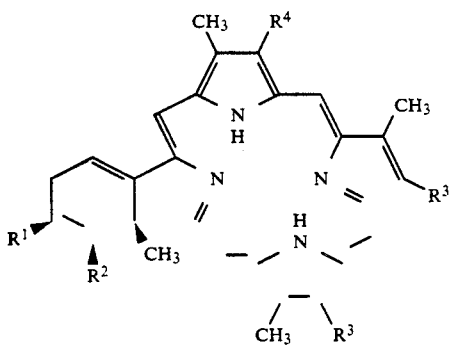

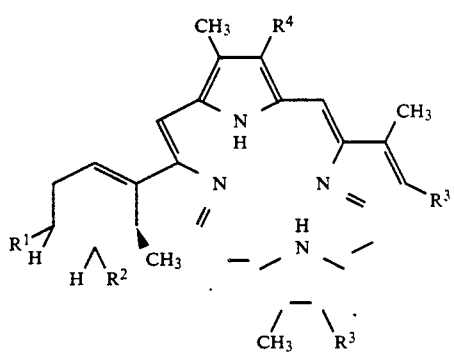

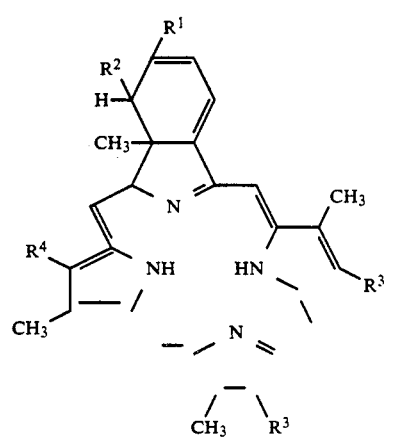

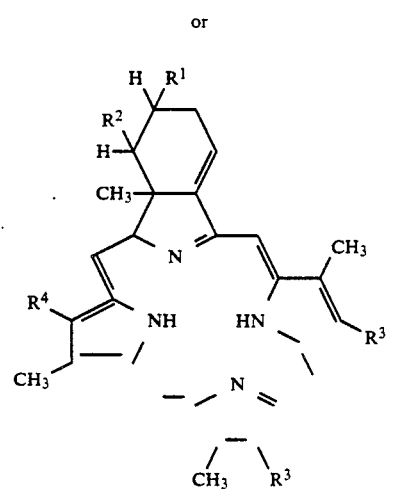

or

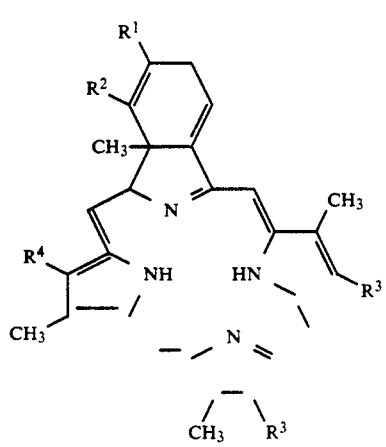

or the metalated and/or labeled form thereof;

wherein each $R^1$ and $R^2$ is independently selected from the group consisting of carbalkoxy (2-6C), alkyl (1-6C) sulfonyl, aryl (6-10C) sulfonyl, aryl (6-10C); cyano; and —CONR$^5$CO— where $R^5$ is aryl (6-10C) or alkyl (1-6C);

each $R^3$ is independently carboxyalkyl (2-6C) or a salt, amide, ester or acylhydrazone thereof, or is alkyl (1-6C); and $R^4$ is CHCH$_2$, —CH$_2$OR$^{4'}$, —CHO, —COOR$^{4'}$, —CH(OR$^{4'}$)CH$_3$, CH(OR$^{4'}$)CH$_2$OR$^{4'}$, —CH(SR$^{4'}$)CH$_3$, —CH(NR$^{4'}_2$)CH$_3$, —CH(CN)CH$_3$, —CH(COOR$^{4'}$)CH$_3$, —CH((OOCR$^{4'}$)CH$_3$, —CH(halo)CH$_3$, or —CH(halo)CH$_2$(halo), wherein $R^{4'}$ is H or alkyl (1-6C) optionally substituted with a hydrophilic substituent, or wherein $R^4$ is an organic group of less than 12C resulting from direct or indirect derivatization of vinyl.

37. A method to detect the presence or absence of malignant cells in a composition selected from the group consisting of bone marrow and a preparation of cells therefrom, which method comprises contacting said composition with Gp for a time sufficient to effect the uptake of said Gp by malignant cells; followed by irradiating said composition with light at a wavelength effective to excite fluorescence of said Gp; and detecting the presence of absence of said fluorescence wherein said Gp is of the formula

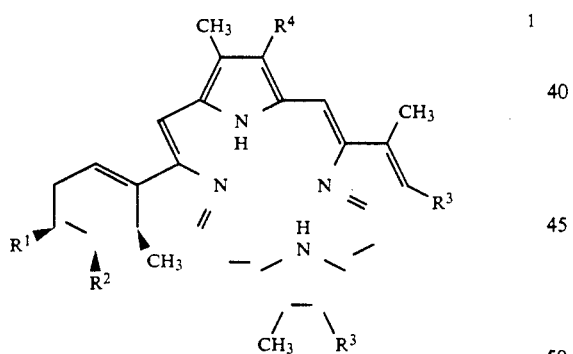

1

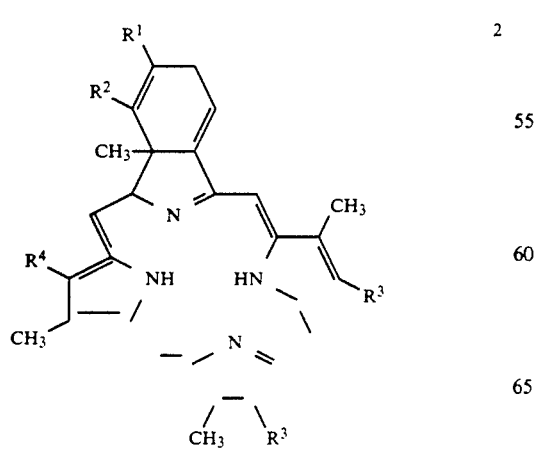

2

-continued

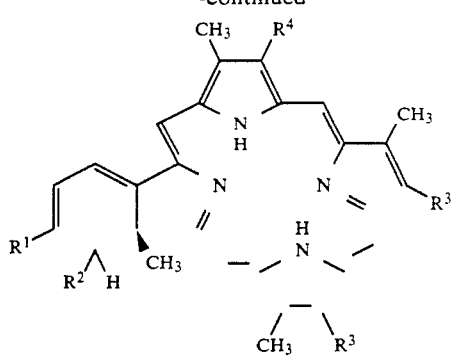

3

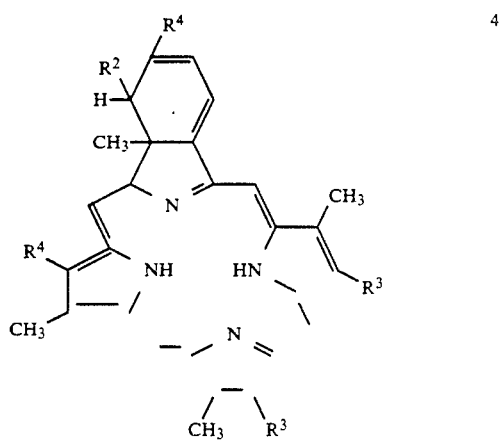

4

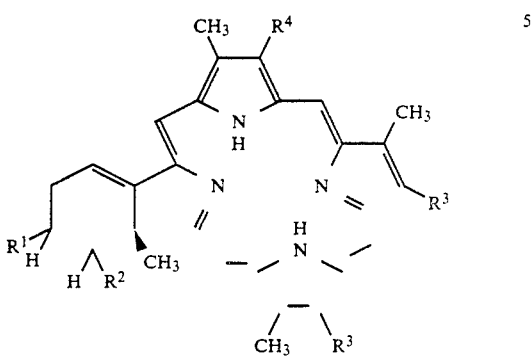

5 or

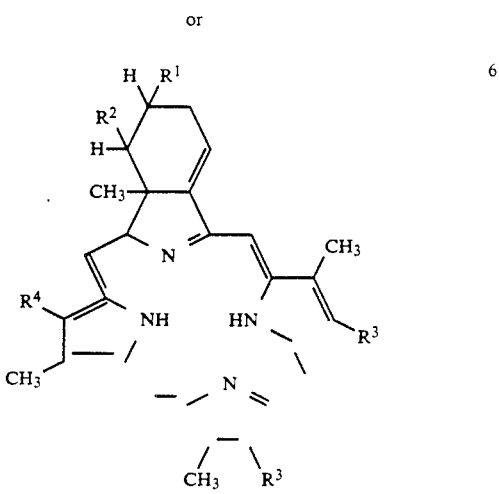

6 or the metalated and/or labeled form thereof;

wherein each $R^1$ and $R^2$ is independently selected from the group consisting of carbalkoxy (2-6C), alkyl (1-6C) sulfonyl, aryl (6-10C) sulfonyl, aryl (6-10C); cyano; and —CONR$^5$CO— where $R^5$ is aryl (6-10C) or alkyl (1-6C);

each $R^3$ is independently carboxyalkyl (2-6C) or a salt, amide, ester or acylhydrazone thereof, or is alkyl (1-6C); and $R_4$ is CHCH$_2$, —CH$_2$OR$^{4'}$, —CHO, —COOR$^{4'}$, —CH(OR$^{4'}$)CH$_3$, CH(OR$^{4'}$)CH$_2$OR$^{4'}$, —CH(SR$_{4'}$)CH$_3$, —CH(NR$^{4'}_2$)CH$_3$, —CH(CN)CH$_3$, —CH(COOR$^{4'}$)CH$_3$, —CH((OOCR$^{4'}$)CH$_3$, —CH(halo)CH$_3$, or —CH(halo)CH$_2$(halo), wherein $R^{4'}$ is H or alkyl (1-6C) optionally substituted with a hydrophilic substituent, or wherein $R^4$ is an organic group of less than 12C resulting from direct or indirect derivatization of vinyl.

* * * * *

UNITED STATES PATENT AND TRADEMARK OFFICE
CERTIFICATE OF CORRECTION

PATENT NO. : 5,087,636

DATED : February 11, 1992

INVENTOR(S) : Jamieson et al.

It is certified that error appears in the above-identified patent and that said Letters Patent is hereby corrected as shown below:

In claim 1, at column 18, line 1 through column 19, line 35, please delete the six chemical formulas shown and substitute therefor the following language:

--depicted in Figures 1-1, 1-2, 1-3, 1-4, 1-5 and 1-6.--

In claim 3, at column 20, lines 27-60, please delete the two chemical formulas shown and substitute therefor the following language:

--depicted in Figures 1-1 and 1-4.--

In claim 19, at column 21, line 55 through column 23, line 18, please delete the six chemical formulas shown and substitute therefor the following language:

--depicted in Figures 1-1, 1-2, 1-3, 1-4, 1-5 and 1-6.--

In claim 21, at column 24, lines 10-43, please delete the two chemical formula shown and substitute therefor the following language:

--depicted in Figures 1-1 and 1-4.--

In claim 25, at column 25, line 35 through column 26, line 66, please delete the six chemical formulas shown and substitue therefor the following language --depicted in Figures 1-1, 1-2, 1-3, 1-4, 1-5 and 1-6.--

UNITED STATES PATENT AND TRADEMARK OFFICE
CERTIFICATE OF CORRECTION

PATENT NO. : 5,087,636
DATED : February 11, 1992
INVENTOR(S) : Jamieson, et al

It is certified that error appears in the above-indentified patent and that said Letters Patent is hereby corrected as shown below:

In claim 37, at column 27, line 36 through column 28, line 66, please delete the six chemical formulas shown and substitute therefor the following language:

--depicted in Figures 1-1, 1-2, 1-3, 1-4, 1-5 and 1-6.--

Signed and Sealed this

Eighth Day of February, 1994

Attest:

BRUCE LEHMAN

Attesting Officer     Commissioner of Patents and Trademarks